US009778259B2

(12) United States Patent
Damiens et al.

(10) Patent No.: US 9,778,259 B2
(45) Date of Patent: Oct. 3, 2017

(54) METHOD FOR DIAGNOSING INVASIVE *CANDIDA* INFECTIONS

(71) Applicants: Bio-Rad Innovations, Marnes la Coquette (FR); Centre Hospitalier Universitaire de Lille, Lille (FR); Universite Lille 2 Droit et Sante, Lille (FR)

(72) Inventors: Sebastien Damiens, Lille (FR); Chantal Fradin, Lille (FR); Daniel Poulain, Tampleuve (FR); Boualem Sendid, Loos (FR); Marc Charles Victor Tabouret, Ennetieres en Weppes (FR)

(73) Assignees: Bio-Rad Innovations, Marnes la Coquette (FR); Centre Hospitalier Universitaire De Lille, Lille (FR); Universite Lille 2 Droit et Sante, Lille (FR)

( * ) Notice: Subject to any disclaimer, the term of this patent is extended or adjusted under 35 U.S.C. 154(b) by 0 days.

(21) Appl. No.: 13/846,900

(22) Filed: Mar. 18, 2013

(65) Prior Publication Data
US 2014/0004538 A1  Jan. 2, 2014

(30) Foreign Application Priority Data
Jun. 29, 2012  (EP) .................................... 12305778

(51) Int. Cl.
G01N 33/569  (2006.01)
(52) U.S. Cl.
CPC ............................. *G01N 33/56961* (2013.01)
(58) Field of Classification Search
None
See application file for complete search history.

(56) References Cited

U.S. PATENT DOCUMENTS

| | | | | |
|---|---|---|---|---|
| 5,288,639 A * | 2/1994 | Burnie | ................... | C07K 14/40 435/320.1 |
| 5,686,248 A | 11/1997 | Burnie et al. | | |
| 7,241,613 B1 * | 7/2007 | Willins | ................... | A61K 36/06 424/184.1 |
| 7,893,219 B2 | 2/2011 | Cassone et al. | | |
| 8,101,406 B2 | 1/2012 | Cassone et al. | | |
| 8,414,889 B2 | 4/2013 | Cassone et al. | | |
| 8,722,727 B2 | 5/2014 | Greenlee et al. | | |
| 2009/0208940 A1* | 8/2009 | O'Connor | ............ | C12Q 1/6895 435/6.13 |
| 2010/0119533 A1 | 5/2010 | Clancy | | |
| 2011/0224228 A1 | 9/2011 | Greenlee et al. | | |

FOREIGN PATENT DOCUMENTS

| | | |
|---|---|---|
| WO | 2006030318 A2 | 3/2006 |
| WO | 2006/109283 A1 | 10/2006 |
| WO | WO 2008109833 A2 * | 9/2008 ............. C07K 14/38 |

OTHER PUBLICATIONS

Pazos et al. 2006 (Diagnostic potential of (1->3)-b-D-glucan and anti-Candida albicans germ tube antibodies for the diagnosis and therapeutic monitoring of invasive candidiasis in neutropenic adult patients; Rev Iberoam Micol 23:209-215).*
Sendid et al. 1999 (New Enzyme Immunoassays for Sensitive detection of Circulation Candida albicans Mannan and Antimannan Antibodies: Useful Combined Test for Diagnosis of Systemic Candidiasis; J Clin Microb 37(5):1510-1517).*
Greenspan et al. 1999 (Defining epitopes: It's not as easy as it seems; Nature Biotechnology, 17:936-937).*
Mikulska et al. 2010 (The use of mannan antigen and anti-mannan antibodies in the diagnosis of invasive candidiasis: recommendations from the Third European Conference on Infections in Leukemia; Crit Care 14(6):1-14).*
Lain et al. 2007 (Diagnosis of invasive candidiasis by enzyme-linked immunosorbent assay using the N-terminal fragment of Candida albicans hyphal wall protein I; BMC Microbiology, pp. 1-11).*
Pepe et al. 2006 (Combining Predictors for Classification Using the Area under the Receiver Operating Characteristic Curve; Biometrics 62: 221-229).*
Sendid et al. 2002 (Combined detection of mannanaemia and anti-mannan antibodies as a strategy for the diagnosis of systemic infection caused by pathogenic Candida species; J. Med. Microbiol. 51:433-442).*
Ponton Jose et al: "Advances and limitations in the early diagnosis of invasive yeasts infections", Revista Iberoamericana de Micologia, vol. 24, No. 3, Sep. 2007 (Sep. 2007), pp. 181-186, XP002682704 (with English summary).
Mitsutake Kotaro et al: "Enolase antigen, mannan antigen, Cand-Tec antigen, and beta-glucan in patients with candidemia", Journal of Clinical Microbiology, vol. 34, No. 8, Aug. 1996, pp. 1918-1921, XP002682705.
Aida Pitarch et al: "Proteomics-based identification of novel Candida albicans antigens for diagnosis of systemic candidiasis in patients with underlying hematological malignancies", Proteomics, vol. 4, No. 10, Oct. 1, 2004 (Oct. 1, 2004), pp. 3084-3106, XP55036868.
Clancy Cornelius J et al: "Immunoglobulin G responses to a panel of Candida albicans antigens as accurate and early markers for the presence of systemic candidiasis.", Journal of Clinical Microbiology, May 2008, Lnkd-PubMed: 18322056, vol. 46, No. 5, May 2008 (May 2008), pp. 1647-1654, XP002682706.

(Continued)

*Primary Examiner* — Gary Nickol
*Assistant Examiner* — Mary Lyons
(74) *Attorney, Agent, or Firm* — Troutman Sanders LLP

(57) ABSTRACT

The present invention concerns an in vitro method for diagnosing invasive candidiasis (IC) in a subject which comprises detecting the presence of a *Candida* glycan and detecting the presence of antibody directed against a protein selected from the group consisting of fructose bisphosphate aldolase (Fba1), enolase 1 (Eno1), heat shock protein 90 (Hsp90), hyphal wall protein (Hwp1), and mannoprotein 65 (Mp65) in a blood, plasma or serum sample of the subject. The invention also relates to a method of determining a suitable treatment regimen for a patient and to a kit for implanting the methods described herein.

16 Claims, 10 Drawing Sheets

(56) References Cited

OTHER PUBLICATIONS

Figure 1:
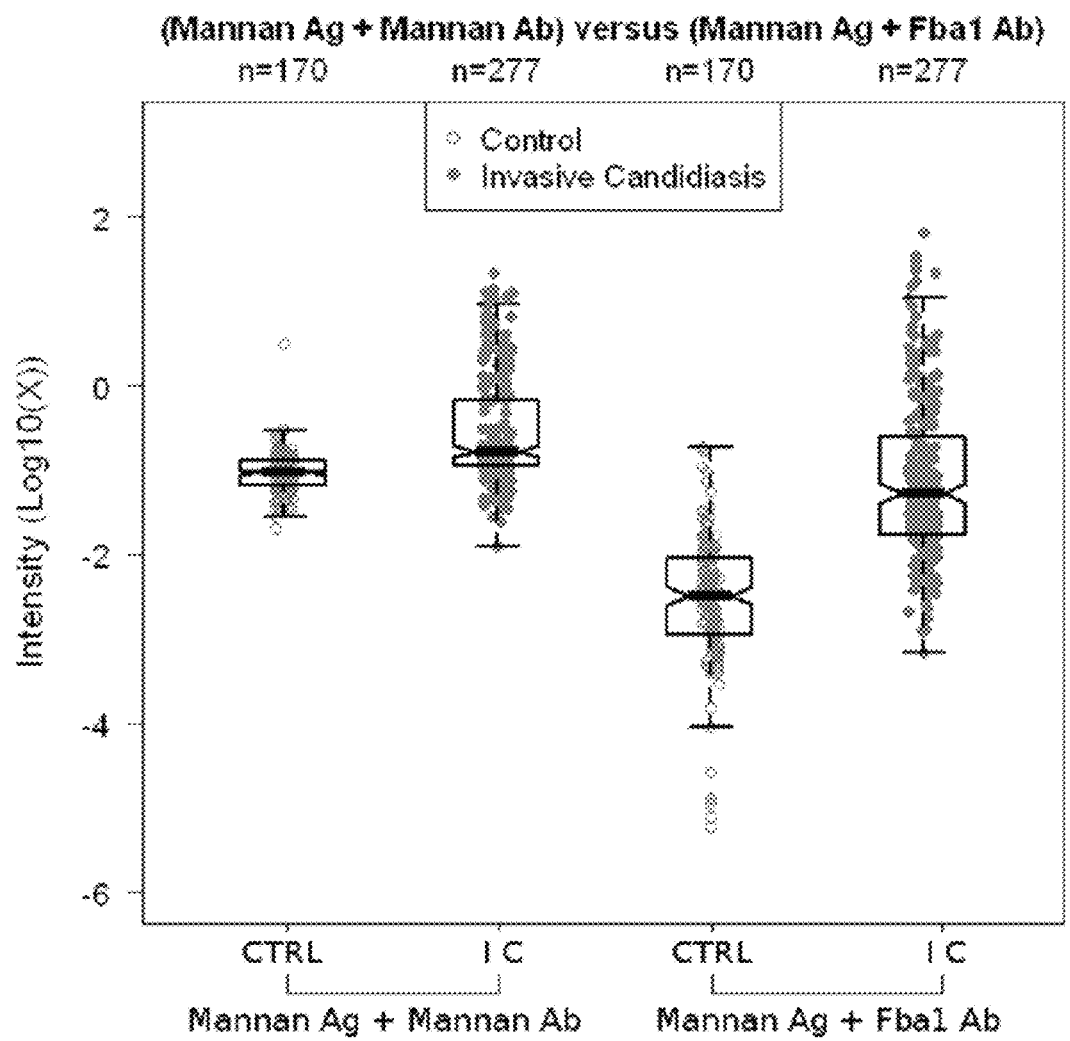

Javier Peman et al: "Current diagnostic approaches to invasive candidiasis in critical care settings", Mycoses, vol. 53, No. 5, Sep. 1, 2010 (Sep. 1, 2010), pp. 424-433, XP55036828.
Boualem Sendid et al: "New enzyme immunoassays for sensitive detection of circulating candida albicans mannan and antimannan antibodies: Useful combined test for diagnosis of systemic candidiasis", Journal of Clinical Microbiology, American Society for Microbiology, Washington, D.C., US, vol. 37, No. 5, May 1, 1999, (May 1, 1999), pp. 1510-1517, XP002971932.
Verduyn Lunel F M et al: "Value of Candida serum markers in patients with invasive candidiasis after myeloblative chemotherapy", Diagnostic Microbiology and Infectious Diseases, Elsevier Science Publishing Co., Amsterdam, NL, vol. 64, No. 4, Aug. 1, 2009 (Aug. 1, 2009), pp. 408-415, XP026348541.
Weig et al: "Genomics and the development of new diagnostics and anti-Candida drugs", Trends in Microbiology, Elsevier Science Ltd., Kidlington, GB, vol. 15, No. 7, Jul. 1, 2007 (Jul. 1, 2007), pp. 310-317, XP022143554.
Pazos Carmen et al: "Diagnostic potential of (1-3)-beta-D-glucan and anti-Candida albicans germ tube antibodies for the diagnosis and therapeutic monitoring of invasive candidiasis in neutropenic adult patients", Revista Iberoamericana de Micologia, vol. 23, 2006, pp. 209-215.
European Search Report, dated Aug. 31, 2012, which issued during the prosecution of European Patent Application No. 12305778.8, to which the present application claims priority.
Ponton Jose et al. "Advances and limitations in the early diagnosis of invasive yeasts infections", Revista Iberoamericana de Micologia, 24(3):181-186, 2007 (with English Translation).
Yeo; Wong et al. "Current Status of Nonculture Methods for Diagnosis of Invasive Fungal Infections", Clinical Microbiology Reviews (2002), vol. 15, No. 03, pp. 465-484.
Weiner; Yount et al., "Mannan Antigenemia in the Diagnosis of Invasive Candida Infections", The Journal of Clinical Investigation (1976), vol. 58, pp. 1045-1053.
Herent; Philippe et al., "Retrospective Evaluation of Two Latex Agglutination Tests for Detection of Circulating Antigens during Invasive Candidos", Journal of Clinical Microbiology (1992), vol. 30, No. 08, pp. 2158-2164.
Switchenko; Arthur C. et al., "An Automated Enzymatic Method for Measurement of D-Arabinitol, a Metabolite of Pathogenic Candida Species", Journal of Clinical Microbiology (1994), vol. 32, No. 01, pp. 92-97.
Fung; Joan et al., "Candida Detection System (CAND-TEC) to Differentiate between Candida albicans Colonization and Disease", Journal of Clinical Microbiology (1986), vol. 24, No. 04, pp. 542-547.
Senn; Laurence et al., "1,3-β-D-Glucan Antigenemia for Early Diagnosis of Invasive Fungal Infections in Neutropenic Patients with Acute Leukemia", Clin. Infect. Dis. (2008), vol. 46, pp. 878-885.
Walsh; Thomas J. et al., "Detection of Circulating Candida Enolase by Immunoassay in patients with Cancer and Invasive Candidiasis", The New England Journal of Medicine (Apr. 11, 1991) vol. 324, No. 15, pp. 1026-1031.
Ellis; Michael et al., "Prospective evaluation of mannan and antimannan antibodies for diagnosis of invasive Candida infections in patients with neutropenic fever", Journal of Medical Microbiology (2009), vol. 58, pp. 606-615.
Staab; Janet F. et al., "Developmental Expression of a Tandemly Repeated, Proline- and Glutamine-rich Amino Acid Motif on Hyphal Surfaces of Candida albicans", The Journal of Biological Chemistry (1996), vol. 271, No. 11, pp. 6298-6305.
Martin; Ronny et al., "Host-pathogen interactions and virulence-associated genes during Candida albicans oral infections", International Journal of Medical Microbiology (2011), vol. 301, No. 05, pp. 417-422.
Hoyer; Lois L. et al., "Candida albicans ALS3 and insights into the nature of the ALS gene family", Curr. Genet. (1998), vol. 33, pp. 451-459.
Green; Clayton B. et al., "Use of Green Fluorescent Protein and Reverse Transcription-PCR to Monitor Candida albicans Aggultinin-Like Sequence Gene Expression in a Murine Model of Disseminated Candidiasis", Infection and Immunity (2005), vol. 73, No. 03, pp. 1852-1855.
Pitarch; Aida et al., "Analysis of the serologic response to systemic Candida albicans infection in a murine model", Proteomics (2001), vol. 1, No. 04, pp. 550-559.
Pitarch; Aida et al., "Reliability of antibodies to Candida methionine synthase for diagnosis, prognosis and risk stratification in systemic candidiasis: A generic strategy for the prototype development phase of proteomic markers", Proteomics Clin. Appl. (2007), vol. 1, No. 10, pp. 1221-1242.
Hernando; Fernando et al., "Identification of protein and mannoprotein antigens of Candida albicans of relevance for the serodiagnosis of invasive candidiasis", International Microbiology (2007), vol. 10, pp. 103-108.
La Valle; Roberto et al., "Generation of a Recombinant 65-Kilodalton Mannoprotein, a Major Antigen Target of Cell-Mediated Immune Response to Candida albicans", Infection and Immunity (2000), vol. 68, No. 12, pp. 6777-6784.
Matthews: Ruth C. et al. "Candida albicans HSP 90: link between protective and auto immunity", Journal Med. Microbiology (1992), vol. 36, pp. 367-370.
Berzaghi; Rodrigo et al., "New Approach for Diagnosis of Candidemia Based on Detection of 65-Kilodalton Antigen", Clinical and Vaccine Immunology (2009), vol. 16, pp. 1538-1545.
Jones; Ted et al., "The diploid genome sequence of Candida albicans", Proc. Natl. Acad. Sci. (2004), vol. 101, No. 19, pp. 7329-7334.
Chibana; Hiroji et al., "Sequence Finishing and Gene Mapping for Candida albicans Chromosome 7 and Syntenic Analysis Against the Saccharomyces cerevisiae Genome", Genetics (2005), vol. 170, No. 4, pp. 1525-1537.
Hopwood; Valerie et al., "A Monoclonal Antibody to a Cell Wall Compnent of Candida albicans", Infection and Immunity (1986), vol. 54, No. 01, pp. 222-227.
Han; Yongmoon et al., "Biochemical Characterization of Candida albicans Epitopes That Can Elicit Protective and Nonprotective Antibodies", Infection and Immunity (1997), vol. 65, No. 10, pp. 4100-4107.
Elguezabal; N. et al., "Inhibition of adherence of Candida albicans and Candida dubliniensis to a resin composite restorative dental material by salivary secretory IgA and monoclonal antibodies", Oral Diseases (2004), vol. 10, pp. 81-86.
Sendid; B. et al., "Antibodies against Glucan, Chitin, and Saccharomyces cerevisiae Mannan as New Biomarkers of Candida albicans Infection That Complement Tests Based on C. albicans Mannan", Clinical and Vaccine Immunology (2008), vol. 15, No. 12, pp. 1868-1877.
Matthews; Ruth et al., "Cloning of a DNA sequence encoding a major fragment of the 47 kilodalton stress protein homologue of Candida albicans", FEMS Microbiology Letters (1989), vol. 60, pp. 25-30.
Xiong; Chengjie et al., "Combining Correlated Diagnostic Tests: Application to Neuropathologic Diagnosis of Alzheimer's Disease", Medical Decision Making (Nov. 2004), vol. 24, No. 6, pp. 659-669.
Liu; Aiyi et al. "On linear combinations of biomarkers to improve diagnostic accuracy", Statistics in Medicine (2005), vol. 24, No. 1, pp. 37-47.
Patterson; Thomas F. MD, "The Role of Echinocandins, Extended-spectrum Azoles, and Polyenes to Treat Opportunistic Moulds and Candida", Current Infectious Disease Reports (2006), vol. 8, No. 06, pp. 442-448.
Pfaller; M. A. et al., "Correlation of MIC with Outcome for Candida Species Tested against Voriconazole: Analysis and Proposal for Interpretive Breakpoints", Journal of Clinical Microbiology (2006), vol. 44, No. 03, pp. 819-826.

(56) References Cited

OTHER PUBLICATIONS

Mean; Marie et al., "Bench-to-bedside review: Candida infections in the intensive care unit", Critical Care (2008), vol. 12, No. 01, p. 204.
Sendid; Boualem et al., "Combined detection of mannanaemia and anti-mannan antibodies as a strategy for the diagnosis of systemic infection caused by pathogenic Candida species", Journal Med. Microbiology (May 2002), vol. 51, No. 5, pp. 433-442.
Ge; Yongchao et al. "Resampling-based Multiple Testing for Microarray Data Analysis", Test (2003), vol. 12, No. 01, pp. 1-77.
Gentleman; Robert C. et al., "Bioconductor: open software development for computational biology and bioinformatics", Genome Biology (2004), vol. 5, Issue 10, p. R80.
Benjamini; Yoav et al., "Controlling the false discovery rate in behavior genetics research", Behavioural Brain Research (2001), vol. 125, pp. 279-284.
Hechenbichler; Schliep et al., "Weighted K-Nearest-Neighbor Techniques and Ordinal Classification", LMU (2004), vol. 399.
International Search Report and Written Opinion Issued in PCT/EP2013/063855 dated Sep. 9, 2013, 10 pages.
International Preliminary Report on Patentability Issued in PCT/EP2013/063855 dated Dec. 31, 2014, 6 pages.
Jacquinot et al., Nature of Candida albicans-Derived Carbohydrate Antigen Recognized by a Monoclonal Antibody in Patient Sera and Distribution Over *Candida* Species, FEMS Microbiology Letters 169 (1998) 131-138.
Chaffin, Candida albicans Cell Wall Proteins, Microbiology and Molecular Biology Reviews, vol. 72, No. 3. 2008, p. 495-544.
Clancy et al., Immunoglobulin G Responses to a Panel of Candida albicans Antigens as Accurate and Early Markers for the Presence of Systemic Candidasis, Journal of Clinical Microbiology, vol. 46, No. 5, 2008, p. 1647-1654.
Mochon et al., Serological Profiling of a Candida albicans Protein Microarray Reveals Permanent Host-Pathogen Interplay and Stage-Specific Responses During Candidemia, Plos Pathog 6(3): E1000827. 2010.
Collot et al., Biotin Sulfone as a New Tool for Synthetic Oligosaccharide Immobilization: Application to Multiple Analysis Profiling and Surface Plasmonic Analysis of Anti-Candida albicans Antibody Reactivity Against Alpha and Beta (1-2) Oligomannosides, J. Med. Chem. 2008, 51, 6201-6210.
Del Bono et al., Clinical Performance of the (1-3)-B-D-Glucan Assay in Early Diagnosis of Nosocomial Candida Bloodstream Infections, Clin. Vaccine. Immunol. 2011, 18(12):2113-2117.
Ellepola et al., Laboratory Diagnosis of Invasive Candidiasis, The Journal of Microbiology, vol. 43, Special Issue (No. S), Feb. 2005, p. 65-84.
Fradin et al., Stage-Specific Gene Expression of Candida albicans in Human Blood, Molecular Microbiology (2003) 47(6), 1523-1543.
Garcia-Ruiz et al., Detection of Antibodies to Candida albicans Germ Tubes for Diagnosis and Therapeutic Monitoring of Invasive Candidiasis in Patients With Hematologic Malignancies, Journal of Clinical Microbiology, vol. 35, No. 12, 1997, p. 3284-3287.
Kofoed et al., Use of Plasma C-Reactive Protein, Procalcitonin, Neutrophils, Macrophage Migration Inhibitory Factor, Soluble Urokinase-Type Plasminogen Activator Receptor, and Soluble Triggering Receptor Expressed on Myeloid Cells-1 in Combination to Diagnose Infections: A Prospective Study, Critical Care 2007, 11: R38.
Kramar et al., MROC: A Computer Program for Combining Tumour Markers in Predicting Disease States, Computer Methods and Programs in Biomedicine 66 (2001), 199-207.
Lain et al., Diagnosis of Invasive Candidiasis by Enzyme-Linked Immunosorbent Assay Using the N-Terminal Fragment of Candida albicans Hyphal Wall Protein 1 BMC Microbiology 2007, 7: 35.
Lain et al., Use of Recombinant Antigens for the Diagnosis of Invasive Candidiasis, Clinical and Developmental Immunology 2008; 2008:721950.
Ma et al., Regularized ROC Method for Disease Classification and Biomarker Selection With Microarray Data, Bioinformatics, vol. 21, No. 24, 2005, pp. 4356-4362.
Martinez et al., Serologic Response to Cell Wall Mannoproteins and Proteins of Candida albicans, Clinical Microbiology Reviews, vol. 11, No. 1, 1998, p. 121-141.
Mikulska et al., The Use of Mannan Antigen and Anti-Mannan Antibodies in the Diagnosis of Invasive Candidiasis: Recommendations From the Third European Conference of Infections in Leukemia, Critical Care 2010, 14: R222.
Nelson et al., Candida Mannan. Chemistry, Suppression of Cell-Mediated Immunity, and Possible Mechanisms of Action Clincal Microbiology Reviews, vol. 4, No. 1, 1991, p. 1-19.
Ostrosky-Zeichner et al., Multicenter Clinical Evaluation of the (1-3) B-D-Glucan Assay as an Aid to Diagnosis of Fungal Infections in Humans, Clinical Infectious Diseases 2005; 41:654-9.
Pepe et al., Combining Predictors for Classification Using the Area Under the ROC Curve, UW Biostatistic Working Paper Series, 2004. <<http://www.bepress.com/uwbiostat/paper196>> Last Accessed Oct. 19, 2015.
Pitarch et al., Decoding Serological Response to Candida Cell Wall Immunome Into Novel Diagnosis, Prognostic, and Therapeutic Candidates for Systemic Candidiasis by Proteomic and Bioinformatic Analyses, Molecular & Cellular Proteomics 5:79-96, 2006.
Podzorski et al., Different Effects of Native Candida albicans Mannan and Mannan-Derived Oligosaccharides on Antigen-Stimulated Lymphoproliferation In Vitro, The Journal of Immunology, vol. 144, No. 2, 1990, 707-716.
Quindos et al., Is there a Role for Antibody Testing in the Diagnosis of Invasive Candidiasis?, Rev Iberoam Micol 2004; 21: 10-14.
Staack et al., Combinded Determination of Plasma MMP2, MMP9, and TIMP1 Improves the Non-Invasive Detection of Transitional Cell Carcinoma of the Bladder, BMC Urology 2006, 6:19.
Su et al., Linear Combinations of Multiple Diagnosis Markers, Journal of the American Statistical Association 88(424): 1350-1355. (1993).
Wang, A Note on Iterative Marginal Optimization: A Simple Algorithm for Maximum Rank Correlation Estimation, Computational Statistics & Data Analysis 51: 2803-2812. (2007).
Wang et al., A Parsimonious Threshold-Independent Protein Feature Selection Method Through the Area Under Revceiver Operating Characteristic Curve, Bioinformatics, vol. 23, No. 20, 2007, pp. 2788-2794.
Wang et al., Identifying Differential Gene Sets Using the Linear Combination of Genes With Maximum AUC, J Proteomics Bioinform 2012, vol. 5(3): 073-083. (2012).
Fradin et al., Beta-1,2 Oligomannose Adhesin Epitopes are Widely Distributed Over the Different Families of Candida albicans Cell Wall Mannoproteins and are Associated Through Both N- and O-Glycosylation Processes, Infection and Immunity, 2008, vol. 76, No. 10, p. 4509-4517.

\* cited by examiner

```
                       SEQUENCE LISTING

<160> NUMBER OF SEQ ID NOS: 29

<210> SEQ ID NO 1
<211> LENGTH: 1080
<212> TYPE: DNA
<213> ORGANISM: Candida albicans
<220> FEATURE:
<221> NAME/KEY: misc_feature
<222> LOCATION: (1)..(1080)
<223> OTHER INFORMATION: Fructose bisphosphate aldolase

<400> SEQUENCE: 1
atggctcctc cagcagtttt aagtaaatcc ggtgttatct acggtaaaga cgtcaaagac      60
ttgtttgact atgctcaaga aaaaggtttt gccattccag ctatcaatgt cacttcatcc     120
tcaactgttg ttgctgcttt agaagctgcc agagacaaca aggctccaat catccttgcaa    180 acttctcaag gtggtgctgc ctactttgcc ggtaaaggtg tcgacaacaa agatcaagct     240
gcttccattg ctggttcaat tgctgccgct cactacatta gagccattgc tccaacttat     300
ggtatcccag ttgttttaca cactgatcac tgtgccaaaa aattattgcc atggtttgat     360
ggtatgttga aagccgatga agaattcttt gctaagaccg gtactccatt gttctcatcc     420
cacatgttgg atttatctga agaaaccgat gacgaaaaca ttgctacttg tgccaaatat     480
ttcgaaagaa tggctaaaat gggtcaatgg ttagaaatgg aaattggtat cactggtggt     540
gaagaagatg gtgtcaacaa cgaacacgtt gaaaaagatg ctttatacac ttctccagaa     600
actgttttcg ctgtctacga atctttacac aagatttctc caaacttttc tattgctgct     660
gcttttggta acgtccacgg tgtttacaaa ccaggtaatg tgcaattgag accagaaatc     720
ttgggtgacc accaagttta cgctaagaaa caaattggta ctgatgctaa cacccatta     780 tacttggttt tccacggtgg ttctggttct actcaagaag aattcaacac tgctatcaag     840
aatggtgttg tcaaggtcaa cttggacact gattgtcaat atgcttactt gactggtatc     900
agagattacg tcaccaacaa gattgaatac ttgaaagcac cagttggtaa cccagaaggt     960
gctgacaaac aaacaagaa atactttgac ccaagagtct gggttagaga aggtgaaaag    1020
accatgtcca agagaattgc tgaagctttg gatattttcc acaccaaagg acaattgtaa    1080

<210> SEQ ID NO 2
<211> LENGTH: 359
<212> TYPE: PRT
<213> ORGANISM: Candida albicans
<220> FEATURE:
<221> NAME/KEY: misc_feature
<222> LOCATION: (1)..(359)
<223> OTHER INFORMATION: Fructose bisphosphate aldolase
```

-continued

<400> SEQUENCE: 2

```
Met Ala Pro Pro Ala Val Leu Ser Lys Ser Gly Val Ile Tyr Gly Lys
1               5                   10                  15

Asp Val Lys Asp Leu Phe Asp Tyr Ala Gln Glu Lys Gly Phe Ala Ile
            20                  25                  30

Pro Ala Ile Asn Val Thr Ser Ser Thr Val Val Ala Ala Leu Glu
        35                  40                  45

Ala Ala Arg Asp Asn Lys Ala Pro Ile Ile Leu Gln Thr Ser Gln Gly
    50                  55                  60

Gly Ala Ala Tyr Phe Ala Gly Lys Gly Val Asp Asn Lys Asp Gln Ala
65                  70                  75                  80

Ala Ser Ile Ala Gly Ser Ile Ala Ala His Tyr Ile Arg Ala Ile
                85                  90                  95

Ala Pro Thr Tyr Gly Ile Pro Val Val Leu His Thr Asp His Cys Ala
            100                 105                 110

Lys Lys Leu Leu Pro Trp Phe Asp Gly Met Leu Lys Ala Asp Glu Glu
        115                 120                 125

Phe Phe Ala Lys Thr Gly Thr Pro Leu Phe Ser Ser His Met Leu Asp
130                 135                 140

Leu Ser Glu Glu Thr Asp Asp Glu Asn Ile Ala Thr Cys Ala Lys Tyr
145                 150                 155                 160

Phe Glu Arg Met Ala Lys Met Gly Gln Trp Leu Glu Met Glu Ile Gly
                165                 170                 175

Ile Thr Gly Gly Glu Glu Asp Gly Val Asn Asn Glu His Val Glu Lys
            180                 185                 190

Asp Ala Leu Tyr Thr Ser Pro Glu Thr Val Phe Ala Val Tyr Glu Ser
        195                 200                 205

Leu His Lys Ile Ser Pro Asn Phe Ser Ile Ala Ala Phe Gly Asn
210                 215                 220

Val His Gly Val Tyr Lys Pro Gly Asn Val Gln Leu Arg Pro Glu Ile
225                 230                 235                 240

Leu Gly Asp His Gln Val Tyr Ala Lys Lys Gln Ile Gly Thr Asp Ala
                245                 250                 255

Lys His Pro Leu Tyr Leu Val Phe His Gly Gly Ser Gly Ser Thr Gln
            260                 265                 270

Glu Glu Phe Asn Thr Ala Ile Lys Asn Gly Val Val Lys Val Asn Leu
        275                 280                 285

Asp Thr Asp Cys Gln Tyr Ala Tyr Leu Thr Gly Ile Arg Asp Tyr Val
290                 295                 300

Thr Asn Lys Ile Glu Tyr Leu Lys Ala Pro Val Gly Asn Pro Glu Gly
305                 310                 315                 320

Ala Asp Lys Pro Asn Lys Lys Tyr Phe Asp Pro Arg Val Trp Val Arg
                325                 330                 335

Glu Gly Glu Lys Thr Met Ser Lys Arg Ile Ala Glu Ala Leu Asp Ile
            340                 345                 350

Phe His Thr Lys Gly Gln Leu
        355
```

<210> SEQ ID NO 3
<211> LENGTH: 1323
<212> TYPE: DNA
<213> ORGANISM: Candida albicans
<220> FEATURE:
<221> NAME/KEY: misc_feature

```
<222> LOCATION: (1)..(1323)
<223> OTHER INFORMATION: Enolase 1

<400> SEQUENCE: 3
atgtcttacg ccactaaaat ccacgccaga tacgtctacg actccagagg taacccaacc      60
gttgaagttg atttcaccac cgacaaaggt ttattcagat caattgtccc atctggtgcc     120
tctactggtg tccacgaagc tttggaattg agagatggtg acaaatccaa atggttaggt     180
aaaggtgttt tgaaagccgt tgccaatgtt aatgacatca ttgccccagc tttaataaaa     240
gccaagatcg atgttgtcga ccaagctaag attgatgaat tcttgttgtc cttggacggt     300
actccaaaca atccaaatt gggtgccaat gctatcttgg gtgtttcttt ggctgctgcc     360
aatgctgccg ctgctgctca aggcattcca ttgtacaaac acattgccaa catttccaat     420
gccaagaaag gtaaattcgt tttgccagtt ccattccaaa acgttttgaa cggtggttcc     480
catgctggtg gtgctttagc tttccaagaa tttatgattg ccccaactgg tgtctccact     540
ttctctgaag ctttgagaat tggttcagaa gtttaccaca acttgaaatc tttgaccaag     600
aagaaatacg gtcaatccgc tggtaacgtc ggtgacgaag gtggtgttgc tccagatatc     660
aaaactccaa aggaagcttt ggacttgatc atggatgcca ttgacaaagc cggttacaaa     720
ggtaaggttg gtattgccat ggatgttgct tcatctgaat tctacaagga cggtaaatac     780
gacttggact ttaaaaaccc agaatccgac ccatctaaat ggtgtctgg cccacaattg     840
gctgactat atgaacaatt gatttccgaa tacccaattg ttctctattga agatccattc     900
gctgaagatg actgggatgc ttgggtccac ttctttgaaa gagttggtga caagatccaa     960
attgtcggtg atgatttgac tgtcactaac cctaccagaa tcaagactgc cattgaaaag    1020
aaagccgcta atgctttgtt gttgaaggtt aaccaaattg gtactttgac tgaatctata    1080
caagctgcta acgattctta cgctgctggt tggggtgtca tggtttccca cagatccggt    1140
gaaaccgaag atactttcat tgctgacttg tcagttggtt taagatctgg tcaaatcaag    1200
actggtgctc cagctagatc tgaaagattg gccaaattga accaaatctt gagaatcgaa    1260
gaagaattag ttctgaagc tatctacgct ggtaaagatt ccaaaaggc ttctcaattg    1320
taa                                                                 1323

<210> SEQ ID NO 4
<211> LENGTH: 440
<212> TYPE: PRT
<213> ORGANISM: Candida albicans
<220> FEATURE:
<221> NAME/KEY: misc_feature
<222> LOCATION: (1)..(440)
<223> OTHER INFORMATION: Enolase 1

<400> SEQUENCE: 4

Met Ser Tyr Ala Thr Lys Ile His Ala Arg Tyr Val Tyr Asp Ser Arg
1               5                   10                  15

Gly Asn Pro Thr Val Glu Val Asp Phe Thr Thr Asp Lys Gly Leu Phe
            20                  25                  30

Arg Ser Ile Val Pro Ser Gly Ala Ser Thr Gly Val His Glu Ala Leu
        35                  40                  45

Glu Leu Arg Asp Gly Asp Lys Ser Lys Trp Leu Gly Lys Gly Val Leu
    50                  55                  60

Lys Ala Val Ala Asn Val Asn Asp Ile Ile Ala Pro Ala Leu Ile Lys
65                  70                  75                  80

Ala Lys Ile Asp Val Val Asp Gln Ala Lys Ile Asp Glu Phe Leu Leu
```

```
                85                  90                  95
Ser Leu Asp Gly Thr Pro Asn Lys Ser Lys Leu Gly Ala Asn Ala Ile
            100                 105                 110

Leu Gly Val Ser Leu Ala Ala Ala Asn Ala Ala Ala Ala Ala Gln Gly
        115                 120                 125

Ile Pro Leu Tyr Lys His Ile Ala Asn Ile Ser Asn Ala Lys Lys Gly
    130                 135                 140

Lys Phe Val Leu Pro Val Pro Phe Gln Asn Val Leu Asn Gly Gly Ser
145                 150                 155                 160

His Ala Gly Gly Ala Leu Ala Phe Gln Glu Phe Met Ile Ala Pro Thr
                165                 170                 175

Gly Val Ser Thr Phe Ser Glu Ala Leu Arg Ile Gly Ser Glu Val Tyr
            180                 185                 190

His Asn Leu Lys Ser Leu Thr Lys Lys Tyr Gly Gln Ser Ala Gly
        195                 200                 205

Asn Val Gly Asp Glu Gly Gly Val Ala Pro Asp Ile Lys Thr Pro Lys
    210                 215                 220

Glu Ala Leu Asp Leu Ile Met Asp Ala Ile Asp Lys Ala Gly Tyr Lys
225                 230                 235                 240

Gly Lys Val Gly Ile Ala Met Asp Val Ala Ser Ser Glu Phe Tyr Lys
                245                 250                 255

Asp Gly Lys Tyr Asp Leu Asp Phe Lys Asn Pro Glu Ser Asp Pro Ser
            260                 265                 270

Lys Trp Leu Ser Gly Pro Gln Leu Ala Asp Leu Tyr Glu Gln Leu Ile
        275                 280                 285

Ser Glu Tyr Pro Ile Val Ser Ile Glu Asp Pro Phe Ala Glu Asp Asp
290                 295                 300

Trp Asp Ala Trp Val His Phe Glu Arg Val Gly Asp Lys Ile Gln
305                 310                 315                 320

Ile Val Gly Asp Leu Thr Val Thr Asn Pro Thr Arg Ile Lys Thr
                325                 330                 335

Ala Ile Glu Lys Lys Ala Ala Asn Ala Leu Leu Leu Lys Val Asn Gln
            340                 345                 350

Ile Gly Thr Leu Thr Glu Ser Ile Gln Ala Ala Asn Asp Ser Tyr Ala
        355                 360                 365

Ala Gly Trp Gly Val Met Val Ser His Arg Ser Gly Glu Thr Glu Asp
    370                 375                 380

Thr Phe Ile Ala Asp Leu Ser Val Gly Leu Arg Ser Gly Gln Ile Lys
385                 390                 395                 400

Thr Gly Ala Pro Ala Arg Ser Glu Arg Leu Ala Lys Leu Asn Gln Ile
                405                 410                 415

Leu Arg Ile Glu Glu Leu Gly Ser Glu Ala Ile Tyr Ala Gly Lys
            420                 425                 430

Asp Phe Gln Lys Ala Ser Gln Leu
        435                 440

<210> SEQ ID NO 5
<211> LENGTH: 2124
<212> TYPE: DNA
<213> ORGANISM: Candida albicans
<220> FEATURE:
<221> NAME/KEY: misc_feature
<222> LOCATION: (1)..(2124)
<223> OTHER INFORMATION: Heat shock protein 90

<400> SEQUENCE: 5
```

```
atggctgacg caaaagttga aactcacgaa ttcactgctg agatctctca gttgatgtct      60
ttgatcatta acacagtcta ttcaaacaag gaaattttct taagagaatt gatctccaat     120
gcttctgatg ctttggacaa aatcagatac caagccttgt ctgatccatc ccaattggaa     180
tccgaaccag aattgttcat tagaatcatc cctcaaaagg accaaaaagt tttggaaatt     240
agagattctg gtattggtat gaccaaagct gacttggtca acaatttggg tactattgct     300
aaatctggta ccaaatcctt tatggaagct ttaagtgctg gtgctgacgt ttctatgatt     360
ggtcaatttg gtgttggttt ctactccttg ttcttggttg ctgatcacgt ccaagttatc     420
tccaaacaca atgacgacga acaatacgtt tgggaatcta cgctggtgg taagttcact     480
gttactttgg atgaaactaa cgaaagattg ggtcgtggta ccatgttgag attgttcttg     540
aaggaagatc aattggaata cttggaagaa aaagaatca agaagttgt caagaaacac     600
tctgaattcg ttgcttatcc aatccaatta gttgtcacca agaagttga aaagaagtt     660
ccagaaaccg aagaagaaga caagctgct gaagaagacg acaagaaacc aaaattggaa     720
gaagtcaagg atgaagaaga cgaaaagaaa gaaaagaaga ccaagactgt caaagaagag     780
gttactgaaa ctgaagagtt gaacaagacc aaaccattat ggaccagaaa cccatctgat     840
atcactcaag atgaatacaa tgcattctac aagtctattt ccaacgactg ggaagaccca     900
ttggctgtca acacttttc tgttgaaggt caattagaat tcagagctat cttgtttgtt     960
ccaagagag ctccatttga tgcctttgaa tccaagaaga agaagaacaa catcaaatta    1020
tacgtccgta gagtgtttat cactgatgat gctgaagagt tgattccaga atggttaagt    1080
ttcatcaagg gggttgtcga ttccgaagac ttgccattga acttgtccag agaaatgttg    1140
caacaaaaca gattttgaa agttatcaga aagaacattg tcaaaaagat gattgaaact    1200
ttcaatgaaa tctctgaaga ccaagagcaa ttcaaccaat tctacactgc tttctccaag    1260
aacatcaaat tgggtattca tgaagatgct caaaacagac aatctttggc taaattgttg    1320
agattctact ctaccaaatc ttctgaagaa atgacttcct tgtctgacta cgttactaga    1380
atgccagaac accaaaagaa tatctactac atcactggtg aatccatcaa agccgttgaa    1440
aaaatcaccat tcttggatgc cttgaaagct aagaactttg aagtcttgtt catggtggat    1500
ccaatcgatg aatatgccat gactcaattg aaggaatttg aagacaagaa attggttgat    1560
attaccaaag actttgaatt ggaagaaagt gacgaagaaa aagctgctag agaaaaggaa    1620
atcaaagaat acgaaccatt gaccaaagct ttgaaagata ttcttggtga tcaagttgaa    1680
aaagttgttg tttcctacaa acttgttgat gctccagctg ccattagaac tggtcaatttt   1740
ggttggtctg ccaatatgga aagaatcatg aaggctcaag ctttgagaga caccaccatg    1800
tcttcttaca tgtcctctaa gaagaccttt gaaatttctc catcttcccc aattatcaag    1860
gaattgaaga gaaagttga aaccgatgga gctgaagaca agaccgttaa ggacttgacc    1920
actttgttgt ttgatactgc attgttgact tctggttttca ccttggacga accatccaac   1980
tttgcccaca gaattaacag attgattgcc ttgggattga atattgacga tgattcagaa    2040
gaaactgctg ttgaacctga agctactact actgcctcaa ctgacgaacc agctggagaa    2100
tctgctatgg aagaagttga ttaa                                          2124
```

<210> SEQ ID NO 6
<211> LENGTH: 707
<212> TYPE: PRT
<213> ORGANISM: Candida albicans
<220> FEATURE:

```
<221> NAME/KEY: misc_feature
<222> LOCATION: (1)..(707)
<223> OTHER INFORMATION: Heat shock protein 90

<400> SEQUENCE: 6

Met Ala Asp Ala Lys Val Glu Thr His Glu Phe Thr Ala Glu Ile Ser
1               5                   10                  15

Gln Leu Met Ser Leu Ile Ile Asn Thr Val Tyr Ser Asn Lys Glu Ile
            20                  25                  30

Phe Leu Arg Glu Leu Ile Ser Asn Ala Ser Asp Ala Leu Asp Lys Ile
        35                  40                  45

Arg Tyr Gln Ala Leu Ser Asp Pro Ser Gln Leu Glu Ser Glu Pro Glu
    50                  55                  60

Leu Phe Ile Arg Ile Ile Pro Gln Lys Asp Gln Lys Val Leu Glu Ile
65                  70                  75                  80

Arg Asp Ser Gly Ile Gly Met Thr Lys Ala Asp Leu Val Asn Asn Leu
                85                  90                  95

Gly Thr Ile Ala Lys Ser Gly Thr Lys Ser Phe Met Glu Ala Leu Ser
            100                 105                 110

Ala Gly Ala Asp Val Ser Met Ile Gly Gln Phe Gly Val Gly Phe Tyr
        115                 120                 125

Ser Leu Phe Leu Val Ala Asp His Val Gln Val Ile Ser Lys His Asn
    130                 135                 140

Asp Asp Glu Gln Tyr Val Trp Glu Ser Asn Ala Gly Gly Lys Phe Thr
145                 150                 155                 160

Val Thr Leu Asp Glu Thr Asn Glu Arg Leu Gly Arg Gly Thr Met Leu
                165                 170                 175

Arg Leu Phe Leu Lys Glu Asp Gln Leu Glu Tyr Leu Glu Glu Lys Arg
            180                 185                 190

Ile Lys Glu Val Val Lys Lys His Ser Glu Phe Val Ala Tyr Pro Ile
        195                 200                 205

Gln Leu Val Val Thr Lys Glu Val Glu Lys Glu Val Pro Glu Thr Glu
    210                 215                 220

Glu Glu Asp Lys Ala Ala Glu Glu Asp Asp Lys Lys Pro Lys Leu Glu
225                 230                 235                 240

Glu Val Lys Asp Glu Glu Asp Glu Lys Lys Glu Lys Lys Thr Lys Thr
                245                 250                 255

Val Lys Glu Glu Val Thr Glu Thr Glu Glu Leu Asn Lys Thr Lys Pro
            260                 265                 270

Leu Trp Thr Arg Asn Pro Ser Asp Ile Thr Gln Asp Glu Tyr Asn Ala
        275                 280                 285

Phe Tyr Lys Ser Ile Ser Asn Asp Trp Glu Asp Pro Leu Ala Val Lys
    290                 295                 300

His Phe Ser Val Glu Gly Gln Leu Glu Phe Arg Ala Ile Leu Phe Val
305                 310                 315                 320

Pro Lys Arg Ala Pro Phe Asp Ala Phe Glu Ser Lys Lys Lys Lys Asn
                325                 330                 335

Asn Ile Lys Leu Tyr Val Arg Arg Val Phe Ile Thr Asp Asp Ala Glu
            340                 345                 350

Glu Leu Ile Pro Glu Trp Leu Ser Phe Ile Lys Gly Val Val Asp Ser
        355                 360                 365

Glu Asp Leu Pro Leu Asn Leu Ser Arg Glu Met Leu Gln Gln Asn Lys
    370                 375                 380

Ile Leu Lys Val Ile Arg Lys Asn Ile Val Lys Lys Met Ile Glu Thr
```

```
                385                 390                 395                 400
            Phe Asn Glu Ile Ser Glu Asp Gln Gly Gln Phe Asn Gln Phe Tyr Thr
                            405                 410                 415
            Ala Phe Ser Lys Asn Ile Lys Leu Gly Ile His Glu Asp Ala Gln Asn
                        420                 425                 430
            Arg Gln Ser Leu Ala Lys Leu Leu Arg Phe Tyr Ser Thr Lys Ser Ser
                    435                 440                 445
            Glu Glu Met Thr Ser Leu Ser Asp Tyr Val Thr Arg Met Pro Glu His
                450                 455                 460
            Gln Lys Asn Ile Tyr Tyr Ile Thr Gly Glu Ser Ile Lys Ala Val Glu
            465                 470                 475                 480
            Lys Ser Pro Phe Leu Asp Ala Leu Lys Ala Lys Asn Phe Glu Val Leu
                            485                 490                 495
            Phe Met Val Asp Pro Ile Asp Glu Tyr Ala Met Thr Gln Leu Lys Glu
                        500                 505                 510
            Phe Glu Asp Lys Lys Leu Val Asp Ile Thr Lys Asp Phe Glu Leu Glu
                    515                 520                 525
            Glu Ser Asp Glu Glu Lys Ala Ala Arg Glu Lys Glu Ile Lys Glu Tyr
                530                 535                 540
            Glu Pro Leu Thr Lys Ala Leu Lys Asp Ile Leu Gly Asp Gln Val Glu
            545                 550                 555                 560
            Lys Val Val Ser Tyr Lys Leu Val Asp Ala Pro Ala Ile Arg
                            565                 570                 575
            Thr Gly Gln Phe Gly Trp Ser Ala Asn Met Glu Arg Ile Met Lys Ala
                        580                 585                 590
            Gln Ala Leu Arg Asp Thr Thr Met Ser Ser Tyr Met Ser Ser Lys Lys
                    595                 600                 605
            Thr Phe Glu Ile Ser Pro Ser Ser Pro Ile Ile Lys Glu Leu Lys Lys
                610                 615                 620
            Lys Val Glu Thr Asp Gly Ala Glu Asp Lys Thr Val Lys Asp Leu Thr
            625                 630                 635                 640
            Thr Leu Leu Phe Asp Thr Ala Leu Leu Thr Ser Gly Phe Thr Leu Asp
                            645                 650                 655
            Glu Pro Ser Asn Phe Ala His Arg Ile Asn Arg Leu Ile Ala Leu Gly
                        660                 665                 670
            Leu Asn Ile Asp Asp Ser Glu Glu Thr Ala Val Glu Pro Glu Ala
                    675                 680                 685
            Thr Thr Thr Ala Ser Thr Asp Glu Pro Ala Gly Glu Ser Ala Met Glu
                690                 695                 700
            Glu Val Asp
            705

<210> SEQ ID NO 7
<211> LENGTH: 1905
<212> TYPE: DNA
<213> ORGANISM: Candida albicans
<220> FEATURE:
<221> NAME/KEY: misc_feature
<222> LOCATION: (1)..(1905)
<223> OTHER INFORMATION: Hyphal wall protein

<400> SEQUENCE: 7
atgagattat caactgctca acttattgct atcgcttatt acatgttatc aattggggcc      60
actgtcccac aggtagacgg tcaaggtgaa acagaggaag ctcttattca aaagagatct     120
tatgattact atcaagaacc atgtgatgat tacccacaac aacaacaaca acaagagcct     180
```

```
tgtgattacc cacaacaaca acagcaggaa gaaccttgtg attacccaca acaacaacca    240
caagagccat gtgactatcc acaacagcca caagaacctt gtgactaccc acaacaacca    300
caagaacctt gtgactaccc acaacaacca caagaacctt gcgacaatcc acctcaacct    360
gatgttcctt gtgacaatcc tcctcaacct gatgttcctt gtgacaatcc tcctcaacct    420
gatattcctt gtgacaatcc tcctcaacct gatattcctt gtgacaatcc tcctcaacct    480
gatcagcctg atgacaatcc tcctattcca aacattccaa ccgattggat tcaaatatt     540 ccaactgatt ggatcccaga tattccagaa agccaacaa ctccagctac tactccaaac     600
attcctgcta caactactac ttctgaatca tcatcttctt cttcttcttc atcatcatct    660
actactccaa aaacttctgc ttcaactaca cctgaatctt ctgttccagc taccactcca    720
aacacttctg ttccaacaac ttcttcagaa tcaactactc cagctactag cccagaaagt    780
tctgttccag ttacttctgg atcatctatt ttagctacca cttcagaatc atcatctgct    840
ccagctacta ctccaaatac atctgttcca accactacta ctgaagccaa atcatcaagt    900
actccattaa ctactactac tgaacatgat acaactgttg tcactgttac ttcatgttct    960
aacagtgttt gtaccgaaag tgaagttact actggtgtta ttgtcatcac atctaaagat   1020
actatttaca ccacttactg tccattgact gaaactactc cagtttctac tgctccagcc   1080
actgaaacac caactggtac agtatccact tctactgaac aatcaactac tgttattact   1140
gttacttcat gttctgaaag ctcttgtacc gaatctgaag ttactactgg tgttgttgtt   1200
gttacttctg aggaaactgt ctacactaca ttctgtccat tgactgaaaa cactccaggt   1260
actgattcaa ctccagaagc ttccattcca cctatggaaa caattcctgc tggttcagaa   1320
tcatccatgc ctgccggtga aacctctcca gctgttccaa atcagatgt tccagctact   1380 gaatcagctc cagttcctga atgactcca gctggttcac aaccatctat tcctgccggt   1440
gaaacctctc cagctgttcc aaaatcagat gttccagcta ctgaatctgc tcctgctcct   1500
gaaatgactc cagctggtac tgaaactaaa ccagctgctc aaaatcatc agctcctgcc   1560 actgaaccct tccccagttgc tccaggtact gaatccgcac cagctggtcc aggtgcttct   1620
tcttctccaa atcttctgt tttggctagt gaaacctcac caattgctcc aggtgctgaa   1680
accgctccag ctggctcaag tggtgctatt actattccgg aatctagtgc tgtcgtctct   1740
acgactgaag gtgctattcc aactacatta gaatcagttc cactcatgca accatctgcc   1800
aattactcaa gtgtcgctcc tatttctaca tttgaaggtg ctggtaacaa catgagattg   1860
actttcggtg ctgctattat tggtattgct gcattcttga tctaa                   1905
```

<210> SEQ ID NO 8
<211> LENGTH: 634
<212> TYPE: PRT
<213> ORGANISM: Candida albicans
<220> FEATURE:
<221> NAME/KEY: misc_feature
<222> LOCATION: (1)..(634)
<223> OTHER INFORMATION: Hyphal wall protein

<400> SEQUENCE: 8

Met Arg Leu Ser Thr Ala Gln Leu Ile Ala Ile Ala Tyr Tyr Met Leu
1               5                   10                  15

Ser Ile Gly Ala Thr Val Pro Gln Val Asp Gly Gln Gly Glu Thr Glu
            20                  25                  30

Glu Ala Leu Ile Gln Lys Arg Ser Tyr Asp Tyr Tyr Gln Glu Pro Cys
        35                  40                  45

```
Asp Asp Tyr Pro Gln Gln Gln Gln Gln Glu Pro Cys Asp Tyr Pro
    50                  55                  60
Gln Gln Gln Gln Gln Glu Pro Cys Asp Tyr Pro Gln Gln Gln Pro
65                  70                  75                  80
Gln Glu Pro Cys Asp Tyr Pro Gln Gln Pro Gln Glu Pro Cys Asp Tyr
            85                  90                  95
Pro Gln Gln Pro Gln Glu Pro Cys Asp Tyr Pro Gln Gln Pro Gln Glu
            100                 105                 110
Pro Cys Asp Asn Pro Pro Gln Pro Asp Val Pro Cys Asp Asn Pro Pro
        115                 120                 125
Gln Pro Asp Val Pro Cys Asp Asn Pro Pro Gln Pro Asp Ile Pro Cys
        130                 135                 140
Asp Asn Pro Pro Gln Pro Asp Ile Pro Cys Asp Asn Pro Pro Gln Pro
145                 150                 155                 160
Asp Gln Pro Asp Asp Asn Pro Pro Ile Pro Asn Ile Pro Thr Asp Trp
            165                 170                 175
Ile Pro Asn Ile Pro Thr Asp Trp Ile Pro Asp Ile Pro Glu Lys Pro
            180                 185                 190
Thr Thr Pro Ala Thr Thr Pro Asn Ile Pro Ala Thr Thr Thr Thr Ser
            195                 200                 205
Glu Ser Ser Ser Ser Ser Ser Ser Ser Ser Ser Thr Thr Pro Lys
    210                 215                 220
Thr Ser Ala Ser Thr Thr Pro Glu Ser Ser Val Pro Ala Thr Thr Pro
225                 230                 235                 240
Asn Thr Ser Val Pro Thr Thr Ser Ser Glu Ser Thr Thr Pro Ala Thr
            245                 250                 255
Ser Pro Glu Ser Ser Val Pro Val Thr Ser Gly Ser Ser Ile Leu Ala
        260                 265                 270
Thr Thr Ser Glu Ser Ser Ser Ala Pro Ala Thr Thr Pro Asn Thr Ser
        275                 280                 285
Val Pro Thr Thr Thr Thr Glu Ala Lys Ser Ser Ser Thr Pro Leu Thr
290                 295                 300
Thr Thr Thr Glu His Asp Thr Thr Val Val Thr Val Thr Ser Cys Ser
305                 310                 315                 320
Asn Ser Val Cys Thr Glu Ser Glu Val Thr Thr Gly Val Ile Val Ile
            325                 330                 335
Thr Ser Lys Asp Thr Ile Tyr Thr Thr Tyr Cys Pro Leu Thr Glu Thr
        340                 345                 350
Thr Pro Val Ser Thr Ala Pro Ala Thr Glu Thr Pro Thr Gly Thr Val
        355                 360                 365
Ser Thr Ser Thr Glu Gln Ser Thr Thr Val Ile Thr Val Thr Ser Cys
    370                 375                 380
Ser Glu Ser Ser Cys Thr Glu Ser Glu Val Thr Thr Gly Val Val Val
385                 390                 395                 400
Val Thr Ser Glu Glu Thr Val Tyr Thr Thr Thr Phe Cys Pro Leu Thr Glu
            405                 410                 415
Asn Thr Pro Gly Thr Asp Ser Thr Pro Glu Ala Ser Ile Pro Pro Met
            420                 425                 430
Glu Thr Ile Pro Ala Gly Ser Glu Ser Ser Met Pro Ala Gly Glu Thr
        435                 440                 445
Ser Pro Ala Val Pro Lys Ser Asp Val Pro Ala Thr Glu Ser Ala Pro
    450                 455                 460
```

Val Pro Glu Met Thr Pro Ala Gly Ser Gln Pro Ser Ile Pro Ala Gly
465                 470                 475                 480

Glu Thr Ser Pro Ala Val Pro Lys Ser Asp Val Pro Ala Thr Glu Ser
                485                 490                 495

Ala Pro Ala Pro Glu Met Thr Pro Ala Gly Thr Glu Thr Lys Pro Ala
            500                 505                 510

Ala Pro Lys Ser Ser Ala Pro Ala Thr Glu Pro Ser Pro Val Ala Pro
            515                 520                 525

Gly Thr Glu Ser Ala Pro Ala Gly Pro Gly Ala Ser Ser Ser Pro Lys
            530                 535                 540

Ser Ser Val Leu Ala Ser Glu Thr Ser Pro Ile Ala Pro Gly Ala Glu
545                 550                 555                 560

Thr Ala Pro Ala Gly Ser Ser Gly Ala Ile Thr Ile Pro Glu Ser Ser
                565                 570                 575

Ala Val Val Ser Thr Thr Glu Gly Ala Ile Pro Thr Thr Leu Glu Ser
                580                 585                 590

Val Pro Leu Met Gln Pro Ser Ala Asn Tyr Ser Ser Val Ala Pro Ile
            595                 600                 605

Ser Thr Phe Glu Gly Ala Gly Asn Asn Met Arg Leu Thr Phe Gly Ala
            610                 615                 620

Ala Ile Ile Gly Ile Ala Ala Phe Leu Ile
625                 630

<210> SEQ ID NO 9
<211> LENGTH: 1137
<212> TYPE: DNA
<213> ORGANISM: Candida albicans
<220> FEATURE:
<221> NAME/KEY: misc_feature
<222> LOCATION: (1)..(1137)
<223> OTHER INFORMATION: Mannoprotein 65

<400> SEQUENCE: 9

```
atgttattca agtctttcgt tacttttact gtcttagcca atgctttggc tgctccatta      60
gctcatcaac atcatcaaca taaagaagaa aaaagagctg ttcatgttgt taccaccacc     120
aatgttgttg ttgtcactat tggtaatggt gatcaaacta ccacttttgc tgctccatct     180
gtagctgctg aatctagtgt tagtgttttct gtcaacactg aaccacctca aaatcatcca     240
actactactc aagatgttgc ttctgcttct acttatccat cttccactga tggttctgcc     300
gcttcttctt ctgctgccgc ttcttcgtct tctcaagctg gttctgaacc ttctggtggt     360
gttggatctg gtggtgctaa aggtattact tattctccat acagtgacaa tggtggatgt     420
aaatcagaat ctcaaattgc cagtgaaatt gctcaattat ctggatttga tgttattcgt     480
ttatacgggg ttgattgtag tcaagttgaa gctgttttaa aagctaaaac ttcatctcaa     540
aaaattttcg ctggtatttt cgatgtttct agtattacat ctggtattga agtttagct      600
gaagccgtta aaagttgcgg tagttgggat gatatttaca ctgtctctat tggtaatgaa     660
ttggttaatg ctggttctgc cactccaagt caaattaaag cttatgttga agaaggtaga     720
aaagctttaa aagctgctgg ttacactggt ccagttgttt ctgttgatac ttttattgct     780
gttattaaca acccagattt atgtgattac tctgattaca tggctgttaa tgctcatgct     840
ttctttgatg gtcacgttgt tgctgaaaac tctggtgctt gggtcttgca acaaatccaa     900
agagtttgga ctgcttgtgg tggtaaaaag aatgttttaa ttactgaaac tggttggcca     960
tctagaggtg attctaatgg tgtcgccgtt ccatctaaga gtaaccaaca agctgctatc    1020
```

```
agttctatta aatcttcttg tggtgcctct gctatattat tcactgcttt caatgacctt    1080
tggaaggccg atggtccata caatgctgaa aaatactggg gtatttactc taactaa        1137
```

<210> SEQ ID NO 10
<211> LENGTH: 378
<212> TYPE: PRT
<213> ORGANISM: Candida albicans
<220> FEATURE:
<221> NAME/KEY: misc_feature
<222> LOCATION: (1)..(378)
<223> OTHER INFORMATION: Mannoprotein 65

<400> SEQUENCE: 10

```
Met Leu Phe Lys Ser Phe Val Thr Phe Thr Val Leu Ala Asn Ala Leu
1               5                   10                  15

Ala Ala Pro Leu Ala His Gln His His Gln His Lys Glu Glu Lys Arg
            20                  25                  30

Ala Val His Val Val Thr Thr Thr Asn Val Val Val Thr Ile Gly
        35                  40                  45

Asn Gly Asp Gln Thr Thr Thr Phe Ala Ala Pro Ser Val Ala Ala Glu
    50                  55                  60

Ser Ser Val Ser Val Ser Val Asn Thr Glu Pro Pro Gln Asn His Pro
65                  70                  75                  80

Thr Thr Thr Gln Asp Val Ala Ser Ala Ser Thr Tyr Pro Ser Ser Thr
                85                  90                  95

Asp Gly Ser Ala Ala Ser Ser Ser Ala Ala Ala Ser Ser Ser Gln
            100                 105                 110

Ala Gly Ser Glu Pro Ser Gly Gly Val Gly Ser Gly Ala Lys Gly
        115                 120                 125

Ile Thr Tyr Ser Pro Tyr Ser Asp Asn Gly Gly Cys Lys Ser Glu Ser
    130                 135                 140

Gln Ile Ala Ser Glu Ile Ala Gln Leu Ser Gly Phe Asp Val Ile Arg
145                 150                 155                 160

Leu Tyr Gly Val Asp Cys Ser Gln Val Glu Ala Val Leu Lys Ala Lys
                165                 170                 175

Thr Ser Ser Gln Lys Ile Phe Ala Gly Ile Phe Asp Val Ser Ser Ile
            180                 185                 190

Thr Ser Gly Ile Glu Ser Leu Ala Glu Ala Val Lys Ser Cys Gly Ser
        195                 200                 205

Trp Asp Asp Ile Tyr Thr Val Ser Ile Gly Asn Glu Leu Val Asn Ala
    210                 215                 220

Gly Ser Ala Thr Pro Ser Gln Ile Lys Ala Tyr Val Glu Glu Gly Arg
225                 230                 235                 240

Lys Ala Leu Lys Ala Ala Gly Tyr Thr Gly Pro Val Val Ser Val Asp
                245                 250                 255

Thr Phe Ile Ala Val Ile Asn Asn Pro Asp Leu Cys Asp Tyr Ser Asp
            260                 265                 270

Tyr Met Ala Val Asn Ala His Ala Phe Phe Asp Gly His Val Val Ala
        275                 280                 285

Glu Asn Ser Gly Ala Trp Val Leu Gln Gln Ile Gln Arg Val Trp Thr
    290                 295                 300

Ala Cys Gly Gly Lys Lys Asn Val Leu Ile Thr Glu Thr Gly Trp Pro
305                 310                 315                 320

Ser Arg Gly Asp Ser Asn Gly Val Ala Val Pro Ser Lys Ser Asn Gln
                325                 330                 335
```

```
Gln Ala Ala Ile Ser Ser Ile Lys Ser Ser Cys Gly Ala Ser Ala Ile
                340                 345                 350

Leu Phe Thr Ala Phe Asn Asp Leu Trp Lys Ala Asp Gly Pro Tyr Asn
            355                 360                 365

Ala Glu Lys Tyr Trp Gly Ile Tyr Ser Asn
        370                 375

<210> SEQ ID NO 11
<211> LENGTH: 1137
<212> TYPE: DNA
<213> ORGANISM: Saccharomyces cerevisiae
<220> FEATURE:
<221> NAME/KEY: misc_feature
<222> LOCATION: (1)..(1137)
<223> OTHER INFORMATION: Scw1

<400> SEQUENCE: 11
atgttattca agtctttcgt tactttact gtcttagcca atgctttggc tgctccatta      60
gctcatcaac atcatcaaca taaagaagaa aaaagagctg ttcatgttgt taccaccacc    120
aatgttgttg ttgtcactat tggtaatggt gatcaaacta ccactttgc tgctccatct    180 gtagctgctg aatctagtgt tagtgttct gtcaacactg aaccacctca aaatcatcca    240
actactactc aagatgttgc ttctgcttct acttatccat cttccactga tggttctgcc    300
gcttcttctt ctgctgccgc ttcttcgtct tctcaagctg ttctgaacc ttctggtggt    360 gttggatctg gtggtgctaa aggtattact tattctccat acagtgacaa tggtggatgt    420
aaatcagaat ctcaaattgc cagtgaaatt gctcaattat ctggatttga tgttattcgt    480
ttatacgggg ttgattgtag tcaagttgaa gctgttttaa aagctaaaac ttcatctcaa    540
aaaattttcg ctggtatttt cgatgttct agtattacat ctggtattga aagtttagct    600
gaagccgtta aaagttgcgg tagttgggat gatatttaca ctgtctctat tggtaatgaa    660
ttggttaatg ctggttctgc cactccaagt caaattaaag cttatgttga agaaggtaga    720
aaagctttaa agctgctgg ttacactggt ccagttgttt ctgttgatac ttttattgct    780
gttattaaca acccagattt atgtgattac tctgattaca tggctgttaa tgctcatgct    840
ttctttgatg gtcacgttgt tgctgaaaac tctggtgctt gggtcttgca acaaatccaa    900
agagtttgga ctgcttgtgg tggtaaaaag aatgttttaa ttactgaaac tggttggcca    960
tctagaggtg attctaatgg tgtcgccgtt ccatctaaga gtaaccaaca agctgctatc   1020
agttctatta atcttcttg tggtgcctct gctatattat tcactgcttt caatgacctt   1080
tggaaggccg atggtccata caatgctgaa aaatactggg gtatttactc taactaa      1137

<210> SEQ ID NO 12
<211> LENGTH: 378
<212> TYPE: PRT
<213> ORGANISM: Saccharomyces cerevisiae
<220> FEATURE:
<221> NAME/KEY: misc_feature
<222> LOCATION: (1)..(378)
<223> OTHER INFORMATION: Scw1

<400> SEQUENCE: 12

Met Leu Phe Lys Ser Phe Val Thr Phe Thr Val Leu Ala Asn Ala Leu
1               5                   10                  15

Ala Ala Pro Leu Ala His Gln His Gln His Lys Glu Glu Lys Arg
            20                  25                  30

Ala Val His Val Val Thr Thr Thr Asn Val Val Val Val Thr Ile Gly
        35                  40                  45
```

```
Asn Gly Asp Gln Thr Thr Thr Phe Ala Ala Pro Ser Val Ala Glu
 50                  55                  60

Ser Ser Val Ser Val Ser Val Asn Thr Glu Pro Pro Gln Asn His Pro
 65                  70                  75                  80

Thr Thr Thr Gln Asp Val Ala Ser Ala Ser Thr Tyr Pro Ser Ser Thr
                 85                  90                  95

Asp Gly Ser Ala Ala Ser Ser Ser Ala Ala Ser Ser Ser Ser Ser Gln
            100                 105                 110

Ala Gly Ser Glu Pro Ser Gly Val Gly Ser Gly Gly Ala Lys Gly
        115                 120                 125

Ile Thr Tyr Ser Pro Tyr Ser Asp Asn Gly Gly Cys Lys Ser Glu Ser
    130                 135                 140

Gln Ile Ala Ser Glu Ile Ala Gln Leu Ser Gly Phe Asp Val Ile Arg
145                 150                 155                 160

Leu Tyr Gly Val Asp Cys Asp Gln Val Ser Ala Val Leu Lys Ala Lys
                165                 170                 175

Thr Ser Ser Gln Lys Ile Phe Ala Gly Ile Phe Asp Val Ser Asn Ile
                180                 185                 190

Ala Ser Gly Ile Glu Ser Leu Ala Glu Ala Val Glu Ala Cys Gly Ser
                195                 200                 205

Trp Asp Asp Ile Tyr Thr Val Ser Ile Gly Asn Glu Leu Val Asn Ala
    210                 215                 220

Gly Ser Ala Thr Pro Ser Gln Ile Lys Ala Tyr Val Asp Glu Gly Arg
225                 230                 235                 240

Lys Ala Leu Lys Ala Ala Gly Tyr Thr Gly Pro Val Val Ser Val Asp
                245                 250                 255

Thr Phe Ile Ala Val Ile Asn Asn Pro Glu Leu Cys Glu Tyr Ser Asp
                260                 265                 270

Tyr Met Ala Val Asn Ala His Ala Phe Phe Asp Gly His Val Ala Ala
    275                 280                 285

Glu Asn Ser Gly Pro Trp Val Leu Gln Gln Ile Gln Arg Val Trp Thr
    290                 295                 300

Ala Cys Ser Gly Lys Lys Asn Val Leu Ile Thr Glu Thr Gly Trp Pro
305                 310                 315                 320

Ser Lys Gly Asp Ser Asn Gly Leu Ala Val Pro Ser Lys Ser Asn Gln
                325                 330                 335

Gln Ala Ala Ile Ser Ser Ile Lys Ser Ser Cys Gly Ala Ser Ala Leu
                340                 345                 350

Leu Phe Thr Ala Phe Asn Asp Leu Trp Lys Ala Asp Gly Pro Tyr Asn
                355                 360                 365

Ala Glu Lys Tyr Trp Gly Ile Tyr Ser Asn
370                 375

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Thr Asp Glu Pro Ala Gly Glu Ser Ala
1               5                   10
```

```
<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Ser Arg Glu Met
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Lys Val Ile Arg Lys
1               5

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Lys Val Ile Arg Lys Asn Ile Val Lys Lys Met Ile Glu
1               5                   10

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
caaggtgaaa cagaggaagc t                                              21

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tcaagcagga atgtttggag tagt                                           24

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atgtcttacg ccactaaaat ccacgc                                         26
```

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttacaattga gaagcctttt ggaaatcttt ac                                     32

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gctcatcaac atcatcaaca t                                                 21

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttagttagag taaataccccc agta                                             24

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atggctcctc cagcagtttt a                                                 21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ttacaattgt cctttggtgt g                                                 21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gatgcaccaa tctcaactga c                                                 21

```
<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ttaaccttga ggagcagtag aagc                                              24

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atggctgacg caaaagttga a                                                 21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ttaatcaact tcttccatag c                                                 21

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 29

His His His His His His
1               5
```

METHOD FOR DIAGNOSING INVASIVE *CANDIDA* INFECTIONS

CROSS-REFERENCE TO RELATED APPLICATION

This application claims priority to European Patent Application 12305778.8 filed Jun. 29, 2012. The entirety of this application is incorporated by reference herein.

SEQUENCE LISTING

The instant application contains a Sequence Listing which has been submitted in ASCII format via EFS-Web and is hereby incorporated by reference in its entirety. Said ASCII copy, created on Jul. 15, 2013, is named 243521.000002_SL.txt and is 42,027 bytes in size.

The present invention concerns an in vitro method for predicting or diagnosing invasive candidiasis (IC) in a subject which comprises detecting the presence of a *Candida* glycan and detecting the presence of antibody directed against a protein selected from the group consisting of fructose biphosphate aldolase (Fba1), enolase 1 (Eno1), heat shock protein 90 (Hsp90), hyphal wall protein (Hwp1), and mannoprotein 65 (Mp65) in a blood, plasma or serum sample of the subject. The invention also relates to a method of determining a suitable treatment regimen for a patient and to a kit for implanting the methods described herein.

Candidiasis is a fungal infection with yeast(s) of any *Candida* species, of which *Candida albicans* is the most common. Candidiasis encompasses infections that range from superficial infections of skin and mucosal membranes, which cause local inflammation and discomfort, to systemic or invasive candidiasis (IC). *Candida* infections of the latter category are also referred to as deep-seated tissue infection affecting one or multiple organ(s) revealed or not by blood culture (candidemia). This severe forms of the disease are usually confined to severely immunocompromised persons, such as cancer, transplant, and AIDS patients, but may occur also in medical and surgical intensive care units and intravenous catheter bearing patients.

Invasive candidiasis remains a problem of public health persisting in medical and surgical intensive care units, onco-haematology, bone marrow and hematopoietic stem cell transplantation and premature newborns wards. According to recent reports *Candida* spp. rank as the fourth most common cause of nosocomial bloodstream infections and are characterized by an important medical and economic impact linked to difficulties of the clinical and biological diagnosis. Systemic candidiasis is associated with long hospital stays and mortality rates of 18 to 70% and a shift in the spectrum of infecting species has also occurred. Non-*Candida albicans* species, although they may have a lower intrinsic pathogenic potential than *C. albicans*, are now identified in more than 45-60% of episodes of hematogenously disseminated candidiasis. Moreover, the increased morbidity as a consequence of candidemia generates important extra costs related to longer hospital stays and prophylactic, empirical, or curative antifungal treatment. While the availability of new antifungal drugs such as echinocandins and new azoles is a promising step toward improving outcomes for patients with invasive candidiasis, a definitive and early diagnostic approach is imperative to avoid delay in the initiation of treatment for infected patients and to prevent unnecessary therapy in high-risk individuals who are only colonized. This delay in the initiation of appropriate antifungal treatment is a cause for the high morbi-mortality rates of IC and is related to a lack of rapid and reliable tests discriminating patients with IC from patients with superficial colonization.

Histological examination of biopsies and blood culture are still considered as the "gold standard" for the diagnosis of IC; however these methods are rarely performed or poorly sensitive, respectively.

Several rapid, non culture based methods have been developed including the detection of anti-Candida antibody against immunogenic targets and the detection of circulating *Candida* antigen (Yeo and Wong. Clin Microbiol Rev 2002; 15:465-84). However, only a few assays have been standardized and are commercially available. The antigen assays target the detection of mannan (Weiner and Yount. J Clin Invest 1976; 58:1045-53; Herent et al. J Clin Microbiol 1992; 30:2158-64), D/L arabinitol (Switchenko et al. J Clin Microbiol 1994; 32:92-7), heat labile antigen (Fung et al. J Clin Microbiol 1986; 24:542-7) and (1→3)-β-D-glucans (Ostrosky-Zeichner et al. Clin Infect Dis 2005; 41:654-9; Senn et al. Clin Infect Dis 2008; 46:878-85). Another assay targeting Enolase has been abandoned (Walsh T J et al. N Engl J Med. 1991 Apr. 11; 324(15):1026-31). Antibody assays target the mannan, the major antigenic component of the yeast cell wall. However, these non-culture methods, even helpful, exhibit numerous drawbacks in their sensitivity and specificity, and sometimes require the combination of two or more assay results for accurate diagnosis of IC.

Improvement of specificity has been obtained by combining the detection of serum mannan and anti-mannan antibodies (Sendid et al. J Clin Microbiol 1999; 37:1510-7). Such an improvement can be explained by the fact that when a specific antigen and antibodies to this antigen are detected in a same patient, the antibodies may facilitate the clearance of the antigen. A recent meta-analysis study of diagnostic values of these two assays has been recently published (Mikulska et al. Crit Care. 2010; 14(6):R222). The use of mannan antigen and anti-mannan antibodies in the diagnosis of invasive candidiasis: recommendations from the Third European Conference on Infections in Leukemia. Detection of mannan appears to be very specific: 93% on 767 patients (11 studies) with a thin 95% IC (91%-94%). However the sensitivity is weak: 58% on 453 patients from 14 studies (95% IC: 53%-62%). Addition of the detection of anti-mannan antibodies allowed to increase the sensitivity up to 83% (95% IC: 79%-87%) but lowered the specificity to 72% due to the lower specificity of anti mannan antibodies detection especially in heavily colonized patients (Ellis et al. J Med Microbiol 2009; 58:606-15).

Many additional proteins that could help in the diagnosis of IC have been pointed out during the past 10 years especially with the development of proteomics analysis. Some of them seem to be specific to pathogenic process. Indeed, more than twenty *Candida* proteins have been reported to be over expressed during the switch saprophytic/pathogenic phases leading to investigate their values for the diagnosis of IC (Clancy et al. J Clin Microbiol 2008; 46:1647-54). The diagnostic value has not been confirmed for the majority of these identified proteins and only primary results on non standardized or sophisticated assay have been obtained for the others. Hyphal Wall Protein (Hwp1) [Staab et al. J Biol Chem 1996; 271:6298-305; Lain et al. BMC Microbiol 2007; 7:35; Martin et al. Int J Med Microbiol; 301:417-22], Agglutinin like sequence family (Als3) [Martin et al. Int J Med Microbiol; 301:417-22; Hoyer et al. Curr Genet 1998; 33:451-9; Green et al. Infect Immun 2005; 73:1852-5], Superoxide dismutase (Sod) [Martin et al. Int J Med Microbiol; 301:417-22], Methionine synthetase—Met6

[Pitarch et al. Proteomics 2001; 1:550-9; Pitarch et al. Proteomics 2004; 4:3084-106; Pitarch et al. Proteomics Clin Appl 2007; 1:1221-42], Malate deshydrogenase [Hernando et al. Int Microbiol 2007; 10:103-8], Fructose biphosphate aldolase [Pitarch et al. Proteomics 2001; 1:550-9; Hernando et al. Int Microbiol 2007; 10:103-8], Hsp70 family [La Valle et al. Infect Immun 2000; 68:6777-84; Pitarch et al. Proteomics 2001; 1:550-9], Hsp90 [Matthews R C. J Med Microbiol 1992; 36:367-70; Pitarch et al. Proteomics 2001; 1:550-9], Phosphoglycerate kinase (PGK) [Pitarch et al. Proteomics 2001; 1:550-9; Pitarch et al. Proteomics 2004; 4:3084-106; Hernando et al. Int Microbiol 2007; 10:103-8; Clancy et al. J Clin Microbiol 2008; 46:1647-54], Diacylglycerol kinase catalytic domain [Hernando et al. Int Microbiol 2007; 10:103-8], Glyceraldehyde 3-phosphate dehydrogenase (G3P) [Pitarch et al. Proteomics 2001; 1:550-9], Alcohol Dehydrogenase (ADH1) [Pitarch et al. Proteomics 2001; 1:550-9], Diacylglycerol kinase [Hernando et al. Int Microbiol 2007; 10:103-8], 65 kDa mannoprotein (CamP65) [Berzaghi et al. Clin Vaccine Immunol 2009; 16:1538-45] make part of all these proteins identified by proteomic approaches.

Limited results are available to conclude on the possibility to use these proteins for improving the diagnosis of IC and further prospective studies are required to confirm the usefulness in clinical practice.

The inventors evaluated the diagnostic performances of a panel of ELISA tests detecting total immunoglobulins against six *Candida albicans* recombinant proteins obtained from *E. coli* transfected by specific plasmids containing fructose biphosphate aldolase (Fba1), enolase 1 (Eno1), heat shock protein 90 (Hsp90), hyphal wall protein (Hwp1), mannoprotein 65 (Mp65), and superoxide dismutase 5 (SOD5) *Candida albicans* genes. These tests were compared to the already marketed mannanemia and antimannan antibody tests. The cohort consisted of patients with IC determined by *Candida albicans* (53 patients and 157 sera) or *Candida* non albicans species (40 patients and 142 sera). Control group consisted of 80 blood donors (80 sera) and 90 *Candida* colonized patients (90 sera) without evidence of IC. Preliminary investigations allowed selecting Hsp90, Hwp1, Fba1, Eno1 and Mp65 as the best candidates for further clinical evaluation of their usefulness for the diagnostic of IC.

To improve the diagnostic potential of these biomarkers, a combination with mannan antigenemia was performed. Indeed, with a specificity arbitrarily fixed at 80.0%, mannanemia/anti-recombinant protein antibody (RP-Ab) association, specific sensitivities of Hsp90 Ab, Fba1 Ab, Hwp1 Ab, Eno1 Ab and Mp65 Ab were 80.9%, 83.8%, 83.8%, 79.1% and 75.5%, while combination of mannanemia/antimannan antibodies lead to a sensitivity of 61.7% for IC patients versus controls (blood donors+hospitalized and colonized patients). When the date of positivity of RP-Ab/mannanemia was compared to the date of positive blood culture, the mean delay of 5 days before isolation of *Candida* species from blood was observed for all RP-Ab biomarkers.

Altogether, these results indicate that anti-Hsp90, anti-Fba1, anti-Hwp1, anti-Eno1 or anti-Mp65 Ab/mannanemia association can advantageously substitute anti-mannan antibodies/mannanemia for the prediction or early diagnosis of IC. Such a result was unexpected because whereas detection of mannan and anti-mannan antibodies is complementary in patients with invasive candidiasis, most probably due to the implication of anti-mannan antibodies in the clearance of soluble mannan, such a complementarity could not be expected for mannan and anti-Hsp90, anti-Fba1, anti-Hwp1, anti-Eno1 or anti-Mp65 antibody, based on a mechanism of antigen clearance. Therefore, it was entirely surprising that specificity and sensitivity of diagnostic of candidemia could be improved by replacing detection of anti-mannan antibodies by detection antibodies against Hwp1, Eno1, Fba1, Hsp90 or Mp65.

Method for Diagnosing Invasive Candidiasis

The invention relates to an in vitro method for diagnosing invasive candidiasis (IC) in a subject, said method comprising, or consisting of, the steps consisting of:

a) detecting the presence of a *Candida* glycan in a blood, plasma or serum sample of the subject;

b) detecting the presence of antibody directed against a *Candida* protein selected from the group consisting of fructose bisphosphate aldolase (Fba1), enolase 1 (Eno1), heat shock protein 90 (Hsp90), hyphal wall protein (Hwp1), and mannoprotein 65 (Mp65) in a blood or plasma sample of the subject; and c) wherein the presence of said *Candida* glycan and/or of said antibody directed against a protein selected from the group consisting of Fba1, Eno1, Hsp90, Hwp1, and Mp65, is indicative of IC.

"Invasive candidiasis" or "IC" is also called candidemia and denotes systemic infection with yeast(s) of any *Candida* species, e.g. *Candida albicans, Candida parapsilosis, Candida kruseï, Candida tropicalis, Candida glabrata, Candida lusitaniae, Geotrichum capitatum, Candida norvegiensis*, and *Candida guillermondii. Candida albicans* is the most common *Candida* species. IC may be ultimately diagnosed by histological examination of biopsies and detection of *Candida* species in blood cultures.

Preferably, invasive candidiasis is due to infection with a *Candida* species selected from the group consisting of *Candida albicans, Candida parapsilosis, Candida kruseï, Candida tropicalis, Candida glabrata, Candida lusitaniae, Geotrichum capitatum*, and *Candida norvegiensis*.

Therefore, a *Candida* glycan and/or a *Candida* protein may be preferably a glycan and/or protein which is found in one or more *Candida* species selected from the group consisting of *Candida albicans, Candida parapsilosis, Candida kruseï, Candida tropicalis, Candida glabrata, Candida lusitaniae, Geotrichum capitatum*, and *Candida norvegiensis*

A "subject" or "patient" may be a human or a non human mammal, such as monkeys, dogs, cats, guinea pigs, hamsters, rabbits, cows, horses, goats and sheep. Preferably, the subject is a human, in particular a man, a woman or a child (0-18 year old).

By "detecting the presence" of an antigen or antibody, it is meant that in the largest extent it is determined in the antigen or antibody is present or absent in the sample to be analysed. According to an embodiment, the level of said *Candida* glycan and/or antibody directed against said *Candida* protein is detected.

Accordingly, the method may comprise or consists of the steps consisting of:

a) detecting the level of a *Candida* glycan in a blood, plasma or serum sample of the subject;

b) detecting the level of antibody directed against a *Candida* protein selected from the group consisting of fructose biphosphate aldolase (Fba1), enolase 1 (Eno1), heat shock protein 90 (Hsp90), hyphal wall protein (Hwp1), and mannoprotein 65 (Mp65) in a blood, plasma or serum sample of the subject; and c) wherein an elevated level of said *Candida* glycan, and/or an elevated level of said antibody directed against said *Candida* protein selected from the group consisting of Fba1, Eno1, Hsp90, Hwp1, and Mp65, relative to a reference level is indicated of invasive candidiasis.

As used herein, a "*Candida* glycan" denotes an oligosaccharide or polysaccharide component of the cell wall of a *Candida* species. Carbohydrates account for 80 to 90% (wt/wt) of the cell wall of *Candida albicans*. The major carbohydrates are (i) mannan, i.e. polymers of mannose in a variety of α and β linkage arrangements which are covalently associated with proteins to form glycoproteins also known as mannoproteins. The term "mannan" is also used to refer to the main soluble immunodominant component present in the outer cell wall layer of *Candida* species. A representative structure of *Candida albicans* mannan has been described in Martinez et al. Clinical Microbiology Reviews, 1998, 11(1), 121-141. Mannan is made up of three major sugar components: the longer outer chain, the N-linked inner core attached to the polypeptide, and the shorter O-glycosidically linked or base labile oligosaccharides attached to the polypeptide. The mannose polymers are linked to proteins by N-glycosidic bonds (through two GlcNAc [di-N-acetylchitobiose] units) to asparagine residues and by O-glycosidic, alkali-labile linkages to threonine or serine residues. The N-glycosidically linked carbohydrate has a backbone chain of α-1,6-linked mannopyranosyl residues with oligosaccharide branches containing mannopyranosyl residues with α-1,2, α-1,3, β-1,2, β-1,4 and single α-1,6-linked mannose units and phosphodiester bonds. Single mannose residues and short, unbranched mannose oligosaccharides constitute the O-glycosidically linked sugar component;

(ii) β-glucans, i.e. polymers of glucose, in particular branched polymers, containing β-1,3 and β-1,6 linkages. The β-glucans include in particular (1,3)-β-D-glucan; and (1,6)-β-D-glucan;

(iii) chitin, which is an unbranched homopolymer of N-acetyl-D-glucosamine (GlcNAc).

By "detecting the presence or level of a *Candida* glycan", it is meant that the presence or level of at least one *Candida* glycan is detected. According to an embodiment, a presence or level of a *Candida* glycan which is determined may be the presence or level of mannan, β-glucan (in particular (1,3)-β-D-glucan), or chitin. In particular, the presence or level of a *Candida* glycan which is determined may be the presence or level of mannan, only. Although characterization of the assay has shown that combinations of more than two of the markers defined herein (*Candida* glycan and antibody directed against a *Candida* protein as recited above) did not significantly improved discriminatory potency of the method, the presence or level of more than one *Candida* glycan could nevertheless be determined, for instance the presence or level of mannan and the presence or level of at least one β-glucan (in particular (1,3)-β-D-glucan), or the presence or level of mannan and the presence or level of chitin, or the presence or level of at least one β-glucan (in particular (1,3)-β-D-glucan) and the presence or level chitin.

The "presence or level of a *Candida* glycan in a blood, plasma or serum sample of the subject" is representative of the presence or level of the *Candida* glycan in circulating blood of the subject. The presence or level of *Candida* glycan may denote in particular the presence or level of soluble *Candida* glycan, as for instance mannan is released from mannoproteins by proteolytic cleavage. Thus, the "presence or level of mannan in a blood, plasma or serum sample of the subject" may denote in particular the presence or level of the soluble immunodominant component of *Candida* mannoproteins, mannan. The detection or level of mannan antigen is also called mannanemia.

The presence or level of a *Candida* glycan may be determined by any suitable chemical or biochemical method known from the one skilled in the art, such as chromatography, enzyme-based chemoluminescent methods, Biacore or mass-spectrometry.

For instance the chromogenic enzymatic test Fungitell® (which is marketed by Associates of Cape Cod Inc.) could be used for detecting (1,3)-β-D-glucan.

Additionally, lectins which bind specifically to chitin, or to (1,3)-β-D-glucan or (1,6)-β-D-glucan, could be used for the detection of chitin, or (1,3)-β-D-glucan or (1,6)-β-D-glucan.

However, as antibody-based methods, which are described in more details below, are preferably used. In this context, immunoassays are particularly suitable The method further includes detecting the presence or level of antibody directed against a *Candida* protein selected from the group consisting of fructose bisphosphate aldolase (Fba1), enolase 1 (Eno1), heat shock protein 90 (Hsp90), hyphal wall protein (Hwp1), and mannoprotein 65 (Mp65) in a blood, plasma or serum sample of the subject.

The presence or level of a *Candida* glycan and of an antibody directed against the *Candida* protein may be detected (i) in one and the same blood, plasma or serum sample of the patient or (ii) in several blood, plasma or serum samples sequentially obtained from the same patient, (iia) either at the same time (i.e. essentially simultaneously or no more than 3 minutes apart) or at least no more than 72 hours, no more than 48 hours, no more than 24 hours, preferably no more than 12 hours, preferably no more than 6 hours, still preferably no more than 3 hours apart, or (iib) in the course of patient monitoring, e.g. 1, 2, 3, 4, 5, 6, 7, 8, 9, 10, 11, 12, 13 or 14 days apart.

The method of the invention is preferably carried out at least twice a week. The method of the invention is also preferably carried out as long as the subject is at risk of developing invasive candidiasis, in particular as long as the patient is hospitalised.

"Fructose bisphosphate aldolase" or "Fba1" is an enzyme involved in glycolysis and gluconeogenesis and which is regulated by yeast-hyphal switch. A representative sequence for Fba1 is Fba1 from *Candida albicans* SC5314 which is encoded for instance by a polynucleotide comprising sequence SEQ ID NO:1, and which consist of the amino acid sequence SEQ ID NO:2. These sequences were published in Jones et al. Proc. Natl. Acad. Sci. U.S.A. 101 (19), 7329-7334 (2004). The diploid genome sequence of *Candida albicans* is available from National Center for Biotechnology Information database under accession number XM_717597 (as available on 14 Feb. 2012).

"Enolase 1" or "Eno1" denotes a glycolytic enzyme (EC 4.2.1.11) present in the cytoplasm and, in minor amounts, in the inner layer of the cell wall of *C. albicans*. A representative sequence for Eno1 is Eno1 from *Candida* SC5314 which is encoded for instance by a polynucleotide comprising sequence SEQ ID NO:3, and which consist of the amino acid sequence SEQ ID NO:4. These sequences were published in Jones et al.; Proc. Natl. Acad. Sci. U.S.A. 101 (19), 7329-7334 (2004). The diploid genome sequence of *Candida albicans* is available from National Center for Biotechnology Information database under accession number XM_706819 (as available on 14 Feb. 2012).

"Heat shock protein 90" or "Hsp90" is a molecular chaperone which is involved, in *Candida albicans*, in the morphogenetic transition from yeast to filamentous growth. Hsp90 has been reported to be present in cell wall of *Candida albicans* and it circulates in body fluids of patients with invasive candidiasis. A representative sequence for Hsp90 is Hsp90 from *Candida* SC5314 which is encoded for instance by a polynucleotide comprising sequence SEQ ID NO:5, and which consist of the amino acid sequence SEQ ID NO:6. These sequences were published in Chibana et al. Genetics 170 (4), 1525-1537 (2005). Sequence finishing and gene mapping for *Candida albicans* are available from National Center for Biotechnology Information database under accession number XM_883730 (as available on 14 Feb. 2012).

"Hyphal wall protein" or "Hwp1" denotes a mannoprotein specifically expressed in the cell wall surface of the hyphae of *C. albicans*. A representative sequence for Hwp1 is Hwp1 from *Candida* SC5314 which is encoded for instance by a polynucleotide comprising sequence SEQ ID NO:7, and which consist of the amino acid sequence SEQ ID NO:8. These sequences were published in Jones et al. Proc. Natl. Acad. Sci. U.S.A. 101 (19), 7329-7334 (2004). The diploid genome sequence of *Candida albicans* is available from National Center for Biotechnology Information database under accession number XM_707905 (as available on 14 Feb. 2012).

"Mannoprotein 65" or "Mp65" denotes a 65-kDa mannoprotein which is present in the cell wall and also in *Candida* culture supernatants and which is thought to have adhesive properties. A representative sequence for Mp65 is Mp65 from *Candida* SC5314 which is encoded for instance by a polynucleotide comprising sequence SEQ ID NO:9, and which consist of the amino acid sequence SEQ ID NO:10. These sequences were published in Jones et al. Proc. Natl. Acad. Sci. U.S.A. 101 (19), 7329-7334 (2004). The diploid genome sequence of *Candida albicans* is available from National Center for Biotechnology Information database under accession number XM_709288 (as available on 14 Feb. 2012).

It is to be understood that *Candida* Fba1, Eno1, Hsp90, Hwp1, and Mp65 proteins are intended to encompass any naturally existing variant or isoform protein differing from the respective representative amino acid sequences identified above by modification of the amino acid sequence and/or of the glycosylation pattern of the protein. By modification of the amino acid sequence it is meant deletion, addition or substitution, of at least one amino acid, for instance by 1 to 15 amino acids, such as by 1, 2, 3, 4, 5, 6, 7, 8, 9 or 10 amino acids. Preferably the variant or isoform protein has at least 80, 85, 87, 90, 91, 92, 93, 94, 95, 96, 97, 98, or 99% sequence identity with the representative amino acid sequence, as can be determined by global pairwise alignment using the Needleman-Wunsch algorithm. The percentage of sequence identity can be readily determined for instance using the program Needle, with the BLOSUM62 matrix, and the following parameters gap-open=10, gap-extend=0.5.

The *Candida* Fba1, Eno1, Hsp90, Hwp1, and Mp65 proteins can elicit antibodies in subjects infected with *Candida* species and developing IC.

The antibodies to be detected may be an IgM, IgD, IgG (in particular IgG$_1$, IgG$_2$, IgG$_3$ or IgG$_4$), IgA and IgE, or any combination thereof.

As used herein, detecting "the presence or level of antibody directed against a *Candida* protein selected from the group consisting of Fba1, Eno1, Hsp90, Hwp1, and Mp65" means that the presence or level of antibodies against at least one of Hsp90, Fba1, Hwp1, Eno1 and Mp65 is detected.

According to an embodiment, the presence or level of antibodies against Fba1, or antibodies against Eno1, or antibodies against Hsp90, or antibodies against Hwp1, or antibodies against Mp65, only, is detected. Although combinations of more than two of the markers defined herein (*Candida* glycan and antibody directed against a *Candida* protein) may not significantly improve discriminatory potency of the method, the presence or level of antibodies against more than one *Candida* protein, in particular 2 or 3 *Candida* proteins, as recited herein may be detected. For instance the presence or level of antibody against Fba1 and the presence or level of antibody against Eno1, or the presence or level of antibody against Fba1 and the presence or level of antibody against Hsp90, or the presence or level of antibody against Fba1 and the presence or level of antibody against Hwp1, or the presence or level of antibody against Fba1 and the presence or level of antibody against Mp65, or the presence or level of antibody against Eno1 and the presence or level of antibody against Hsp90, or the presence or level of antibody against Eno1 and the presence or level of antibody against Hwp1, or the presence or level of antibody against Eno1 and the presence or level of antibody against Mp65, or the presence or level of antibody against Hwp1 and the presence or level of antibody against Mp65.

When the *Candida* protein is a glycoprotein, such as Hwp1, Hsp90 and Mp65, the antibodies directed against a *Candida* protein which are detected or measured may the antibodies binding to a deglycosylated form of said *Candida* protein.

The presence or level of antibody may be determined by any suitable immunoassay method known from the one skilled in the art, as described below.

The method preferably does not include detection of additional biomarkers, other than *Candida* glycan(s) and antibody(ies) directed against a *Candida* protein selected from the group consisting of Fba1, Eno1, Hsp90, Hwp1, and Mp65. In particular, the method preferably does not comprise detecting antibody(ies) directed against *Candida* glycan(s), especially against mannan.

Immunoassay Methods

Immunoassays are antibody-based methods which enable for measuring antigens or antibodies. They typically include indirect, sandwich, or competition immunoassays, for instance in a radioimmunoassays (RIA) or EIA (Enzyme ImmunoAssay) format. A sandwich immunoassay is a method using two antibodies specific for the antigen to be detected, which bind to different sites on the antigen or ligand. The primary antibody (or capture antibody), which recognizes the antigen, is attached to a solid surface. The antigen is then added followed by addition of a second antibody referred to as the detection antibody. The detection antibody binds the antigen to a different or a repeated epitope(s). As the antigen concentration increases the amount of detection antibody increases leading to a higher measured response.

To quantify the extent of binding different reporters can be used: a radioactive tracer in RIA, or a fluorophore or enzyme in EIA (in particular in ELISA). In ELISA, an enzyme is typically attached to the detection antibody or to a third antibody which binds the detection antibody and which must be generated in a different species than detection antibodies (i.e. if the detection antibody is a rabbit antibody than the third antibody would be an anti-rabbit from goat, chicken, etc., but not rabbit). The substrate for the enzyme is added to the reaction that forms a colorimetric readout as the detection signal. The enzyme step of the assay can be replaced with a fluorophore-tagged detection and the fluorescent signal is measured in a fluorescent plate reader. The signal generated is proportional to the amount of target antigen present in the sample.

A competitive binding assay is based upon the competition of labelled and unlabeled antigen for a limited number of antibody binding sites. A fixed amount of labelled antigen and a variable amount of unlabeled antigen are incubated with an antibody bound to a solid phase. The amount of labelled antigen is a function of the total concentration of labelled and unlabeled antigen. As the concentration of unlabeled antigen is increased, less labelled antigen can bind to the antibody and the measured response decreases. Thus the lower the signal, the more unlabeled antigen there is in the sample.

In indirect immunoassay, an antigen is coated onto a solid surface. The coated solid surface is then incubated with a sample to analyse if it contains antibodies specific for the antigen. Detection of antigen-bound antibodies is then performed using a detectably labelled secondary antibody which binds to the antibody specific for the antigen. The secondary antibody may be labelled with a fluorophore which generates a fluorescent signal measurable in a fluorescent plate reader, or with an enzyme which can produce a colorimetric signal upon addition of the enzyme substrate.

The immunoassay may be performed in a lateral flow immunochromatographic assay format, high throughout and/or multiplex immunoassay format such as Luminex®, platform or any microfluidic derived format such as microchip immunoassays, etc. . . .

As used herein, "antibody" or "immunoglobulin" have the same meaning, and are used equally. In natural conventional antibodies, two heavy chains are linked to each other by disulfide bonds and each heavy chain is linked to a light chain by a disulfide bond. There are two types of light chain, lambda ($\lambda$) and kappa $\kappa$. There are five main heavy chain classes (or isotypes) which determine the functional activity of an antibody molecule: IgM, IgD, IgG (such as $IgG_1$, $IgG_2$, $IgG_3$ or $IgG_4$), IgA and IgE. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The specificity of the antibody resides in the structural complementarity between the antibody combining site and the antigenic determinant (epitope). Antibody combining sites are made up of residues that are primarily from the hypervariable or complementarity determining regions (CDRs). Occasionally, residues from non hypervariable or framework regions (FR) influence the overall domain structure and hence the combining site. The CDR refers to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. FR refers to amino acid sequences interposed between CDRs.

Antibodies may be monoclonal antibodies (mAb), polyclonal antibodies, or fragment thereof. Monoclonal antibodies are monospecific antibodies, produced by clones of a hybridoma cell line, which bind to the same epitope on an antigen. Polyclonal antibodies are a combination of immunoglobulins directed against a specific antigen, each immunoglobulin possibly binding to a different epitope on the antigen. Polyclonal antibodies are generally produced by immunisation of a suitable mammal, such as a mouse, rabbit or goat. Antibody fragments include for instance Fab, Fab', $F(ab')_2$, Fv, scFv, and nanobodies (single chain antibodies).

For the detection of a *Candida* glycan, antibodies binding preferentially or specifically to said *Candida* glycan may be used. The antibodies which may be used for the detection of a *Candida* glycan may be monoclonal antibodies (mAb), polyclonal antibodies, or fragment thereof.

As used herein, an antibody binding "preferentially" to said *Candida* glycan, is an antibody showing less that 15% cross reactivity, preferably less than 10% or 5% cross reactivity, with an antigen different from said *Candida* glycan. An antibody binding "specifically" to said *Candida* glycan is an antibody showing no cross-reactivity with any other antigen.

For the detection of mannan, antibodies binding to $\alpha$-1,2-linked oligomannose sequences of more than four residues, or to $\beta$-1,2-linked oligomannosides could be used for instance. The monoclonal antibody EBCA1, which is available in the Platelia *Candida* antigen and Platelia *Candida* antigen Plus (Ag) tests (Bio-Rad Laboratories, Marnes La-Coquette, France), binds to a minimal epitope consisting of $\alpha$-1,2-linked oligomannose sequences of more than four (or at least five) residues which are present in the acid-stable fraction of mannan. Other monoclonal antibodies could be used for the detection of $\beta$-1,2-linked oligomannosides, such as antibody 5B2 which preferentially binds with mannobiosides (Hopwood et al. Infect. Immun. 1986, 54, 222-227; Collot M et al J. Med. Chem. 2008; 51:6201-6210), antibody B6.1 which specifically binds with mannotriose (Han, Y et al. Infect. Immun. 1997; 65:4100.) and antibody 26G7 which recognizes an heteropolymer 2 beta and 2 alpha mannosides (Elguezabal et al., Oral Dis, 2004, 10, 81-86).

In particular, mannan may be conveniently detected by a sandwich enzyme immunoassay which uses, as capture and detection antibodies, an antibody recognizing sequences of $\alpha$-linked oligomannoses constituted of more than four (or at least five) residues, such as the monoclonal antibody EBCA1.

$\beta$-glucans and chitin are immunogenic as circulating anti-$\beta$-D-glucans and anti-chitin antibodies have been found in humans (Sendid et al. Clin. Vaccine Immunol. 2008, 15, 1868-1877). Accordingly antibodies can be elicited against (1,6)-$\beta$-D-glucan, (1,3)-$\beta$-D-glucan or chitin in order to be used in an immunoassay for detecting a (1,6)-$\beta$-D-glucan or chitin.

For the detection of (1,3)-$\beta$-D-glucan and/or (1,6)-$\beta$-D-glucan, an antibody such as antibody 2G8 which was described in the international patent application WO2006/030318, or an anti-(1,3)-$\beta$-D-glucan antibody such as available from Biosupplies Australia Pty. Ltd. may be used.

For the detection of antibody(ies) directed against a *Candida* protein, purified *Candida* protein, or epitopic fragments thereof, or a polypeptide comprising full length protein, epitopic fragments or variants thereof which have been recombinantly produced or chemical synthesized may be used. When the *Candida* protein is a glycoprotein, the purified *Candida* protein, or epitopic fragments thereof, may have been deglycosylated. Purified and recombinant full length proteins or epitopic fragments thereof may or may not include glycosylation(s). Preferably the polypeptide used for detection of an antibody directed against a *Candida* protein is devoid of glycosylation.

As used herein, the term "epitopic fragment" refers to a polypeptide fragment of a protein which consists of a stretch of contiguous amino acids of the protein and comprises one or more epitopes of said protein. An epitopic fragment retains the capacity to be bound by at least part, preferably all, of the antibodies that bind to the full length protein from which the fragment is derived. An epitope may be linear when made of contiguous amino acids, or conformational when an antibody binds to discontinuous amino acids that come together in three dimensional conformation. It is generally admitted that a linear epitope is constituted by at least 4 or 5 amino acid contiguous residues. Accordingly, an "epitopic fragment" according to the invention preferably comprises at least 4, 5, 6, 7, 8, 9, 10, 12, 15, 20, 25, 30, 40, 50 or 100 contiguous amino acids of the protein from which the epitopic fragment derives. An "epitopic fragment" may comprise less than 300, 250, 200, 150, 100, 50, 40, 30, 20 or 15 amino acids.

The fragments can be generated for instance by processing the full length protein, or a longer fragment of said protein, with a proteolytic enzyme (classically trypsin, chymotrypsin, or collagenase), or by chemical treatment with cyanogen bromide (CNBr), for instance.

Variant polypeptides of the full length Candida protein or of an epitopic fragment thereof may be obtained by modification of its amino acid sequence by deletion, addition or substitution, of at least one amino acid, for instance by 1 to 15 amino acids, such as by 1, 2, 3, 4, 5, 6, 7, 8, 9 or 10 amino acids. Preferably the variant polypeptide has at least 80, 85, 87, 90, 91, 92, 93, 94, 95, 96, 97, 98, or 99% sequence identity with the full length Candida protein or epitopic fragment thereof, as can be determined by global pairwise alignment using the Needleman-Wunsch algorithm, in particular using the program Needle, with the BLOSUM62 matrix, and the following parameters gap-open=10, gap-extend=0.5. A variant polypeptide retains the capacity to be bound by at least part, preferably all, of the antibodies that bind to the full length protein or the fragment thereof from which it derived. A variant polypeptide may typically comprise a heterologous polypeptide sequence, such as a tag (His-tag, GFP, etc. . . . ) to facilitate purification.

Deglycosylation of Candida (glycol) protein, of fragments thereof, may be performed by any chemical or enzymatic method compatible with the preservation of the antigenicity of the protein (i.e maintaining epitope structures). Reference may be made for instance to trifluoromethanesulfonic acid (TFMS) hydrolysis for complete glycan removal without altering the protein component, or to processing with the enzymes PNGase, or F Endoglycosidases F1, F2, and F3 for removal of N-linked glycans.

Recombinant Candida full length protein, epitopic fragments or variants thereof may be produced by any method known to the one skilled in the art. Typically, a nucleic acid sequence comprising a sequence encoding the desired polypeptide, under the control of or operatively associated with transcriptional and translational control sequences (in particular a promoter sequence) is inserted in an expression vector. A vector is the vehicle by which a DNA or RNA sequence (e.g. a foreign gene) can be introduced into a host cell, so as to transform the host and promote expression (e.g. transcription and translation) of the introduced sequence. Vectors include plasmids, phages, viroses, etc. An "expression system", i.e. the host cell and a compatible vector for the expression of Candida protein, or epitopic fragment thereof, may include E. coli host cells and plasmid vectors, yeast host cells (such as Pichia pastoris) and vectors and plasmid vectors, insect host cells and Baculovirus vectors, and mammalian host cells (such as COS-1 or CHO cells) and vectors. Preferably, recombinant Candida protein or epitopic fragments thereof are produced in E. coli. The recombinant proteins may be produced with tags, such as His-tags, in order to facilitate their purification, which may be eliminated afterwards.

For epitopic fragments preferably containing no more than 20 amino acids, chemical synthesis such as solid phase synthesis may be employed for preparing the epitopic fragments.

It has been reported that a 47-kDa antigen which is a heat-stable breakdown product of Hsp90 may be found in patients with systemic candidiasis. Cloning of this 47-kDa fragment (consisting of amino acids at positions 313 to 707 of Hsp90 sequence SEQ ID NO:6) has been described in Matthews and Burnie, 1989, FEMS Microbiol. Lett. 60:25-30 and in U.S. Pat. No. 5,686,248. It has been further shown that antibodies to the 47-kDa antigen of Hsp90 cross react with peptides of sequences STDEPAGESA (SEQ ID NO:13), LSREM (SEQ ID NO:14), LKVIRK (SEQ ID NO:15) and LKVIRKNIVKKMIE (SEQ ID NO:16). Accordingly, a polypeptide which may be used for detecting anti-Hsp90 antibodies may be selected in particular from the group consisting of a polypeptide comprising, or consisting of:
  a) SEQ ID NO:6 or a naturally existing variant or isoform thereof;
  b) an epitopic fragment of a polypeptide defined in a), in particular a fragment consisting of amino acids at positions 313 to 707 of SEQ ID NO:6, or a variant thereof; and
  c) SEQ ID NO:13, SEQ ID NO:14, SEQ ID NO:15, or SEQ ID NO:16 or a variant thereof.

While full length Hwp1 protein can be used for detecting anti-Hwp1 antibodies, it has been reported that a 161 amino acid long N-terminal fragment thereof (amino acids at positions 41 to 200) increased antibody detection by ELISA in sera of patients with invasive candidiasis (Lain et al., 2007, BMC Microbiology, 7:35). Furthermore, a fragment of Hwp1 consisting of amino acids at positions 27 to 203 of Hwp1 was shown to be an epitopic fragment of Hwp1 (Fradin et al., 2008 Infect. Immun. 76, 4509-4517).

Accordingly, a polypeptide which may be used for detecting anti-Hwp1 antibodies may be selected in particular from the group consisting of a polypeptide comprising, or consisting of:
  a) SEQ ID NO:8 or a naturally existing variant or isoform thereof;
  b) an epitopic fragment of a polypeptide defined in a), in particular a fragment consisting of amino acids at positions 41 to 200, or 27 to 203 of SEQ ID NO:8, or a variant thereof.

A polypeptide which may be used for detecting anti-Fba1 antibodies may be selected in particular from the group consisting of a polypeptide comprising, or consisting of:
  a) SEQ ID NO:2 or a naturally existing variant or isoform thereof;
  b) an epitopic fragment of a polypeptide defined in a), or a variant thereof.

A polypeptide which may be used for detecting anti-Eno1 antibodies may be selected in particular from the group consisting of a polypeptide comprising, or consisting of:
  a) SEQ ID NO:4 or a naturally existing variant or isoform thereof;
  b) an epitopic fragment of a polypeptide defined in a), or a variant thereof.

For the detection of antibodies against Mp65, the Scw1 protein, i.e. the protein homologous to Mp65 in Saccharomyces cerevisiae, may also be used. Scw1 coding sequence and amino acid sequence are shown in SEQ ID NO:11 and 12, respectively. Accordingly, a polypeptide which may be used for detecting anti-Mp65 antibodies may be selected in particular from the group consisting of a polypeptide comprising, or consisting of:
a) SEQ ID NO:10 or a naturally existing variant or isoform thereof, in particular a polypeptide comprising, or consisting of SEQ ID NO:12;
b) an epitopic fragment of a polypeptide defined in a), or a variant thereof.

Diagnosis of Invasive Candidiasis

According to an embodiment, diagnosing invasive candidiasis may be performed by comparing the level of said *Candida* glycan with a reference level, and comparing the level of antibody directed against said *Candida* protein selected from the group consisting of Fba1, Eno1, Hsp90, Hwp1, and Mp65, with another reference level. If an elevated level of said *Candida* glycan, and/or an elevated level of antibody directed against said *Candida* protein selected from the group consisting of Fba1, Eno1, Hsp90, Hwp1, and Mp65, relative to their respective reference level is detected, then the subject is developing or has developed invasive candidiasis. In this embodiment, a combined interpretation of the separated assays is thus performed.

The reference level(s) may be determined as a single value or a range of values which is determined based on the level of said *Candida* glycan or the level of antibody directed against said *Candida* protein, as appropriate, measured in a population of healthy subjects, in a population of subjects superficially infected with a *Candida* strain, or in a population of subjects suffering from invasive candidiasis.

The reference level can also be determined by analysing a sample from the same subject for instance at an earlier time point prior to onset of invasive candidiasis or prior to suspicion of invasive candidiasis.

Typically, the analysed population could be divided into quantiles based on the measured level of antigen or antibody. The reference level could be defined as the median, or the second tertile, or the second or third quartile, or the third or fourth quintile etc. . . .

Comparison with a reference level may also be performed by comparing the level of said *Candida* glycan or the level of antibody directed against said *Candida* protein with the level of *Candida* glycan or antibody, as appropriate, measured in a standard sample constituted by a pool of sera obtained from patients having invasive candidiasis.

The reference level for a given marker may vary depending on the method used for measuring.

According to another embodiment, a combined analysis of the levels of said *Candida* glycan and of said antibody directed against said *Candida* protein is performed in order to determine if the subject has or has not invasive candidiasis. In this embodiment, a combined analysis of the biomarkers is thus performed.

According to this embodiment, the level of a *Candida* glycan and the level of an antibody directed against the *Candida* protein are detected in one and the same blood, plasma or serum sample of the patient or in several blood, plasma or serum samples sequentially obtained from the same patient essentially simultaneously.

Based on the analysis of a reference set of blood, plasma or serum samples from subjects with invasive candidiasis and subjects without invasive candidiasis, a Relative Operating Characteristic (ROC) curve can be generated for each marker analysed. A ROC curve is a graphical representation of the sensitivity (or true positive rate) against the false positive rate (i.e. [1-specificity], specificity being the true negative rate) of a marker-based test. A ROC space is defined by sensitivity and (1-specificity) as x and y axes respectively. The best possible prediction method would yield a point in the upper left corner or coordinate (0,1) of the ROC space, representing 100% sensitivity (no false negatives) and 100% specificity (no false positives). A completely random guess would give a point along a diagonal line (the so-called line of no-discrimination) from the left bottom to the top right corners. The diagonal divides the ROC space. Points above the diagonal represent good classification results (better than random), points below the line poor results (worse than random). The Area Under the Curve (AUC) of a ROC curve may be calculated. The higher the AUC, the higher the diagnostic accuracy of the diagnostic marker.

For combined analysis of markers, such as the level of said *Candida* glycan and the level of said antibody directed against said *Candida* protein, a new virtual marker Z may be calculated based on a linear combination of the levels of the individual markers, i.e. the level of said *Candida* glycan and the level of antibody directed against said *Candida* protein. Z is calculated as follows: $Z=\Sigma a_i \times [Marker_i]$ where $a_i$ are calculated coefficients and $[Marker_i]$ are individual levels of marker (optionally in normalised units). The values of the $a_i$ coefficients are determined in order to maximize the Area Under the Curve (AUC) of the ROC curve for the selected marker combination.

Determination of the coefficient values may be readily achieved using for instance mROC program or any other program implementing an algorithm for maximising the AUC of ROC which may be used for multivariate ROC (Wang, Computational Statistics and Data Analysis 2007; 51:2803-2812; Xiong et al. Med Decis Making. 2004 November-December; 24(6):659-69; Ma and Huang, Bioinformatics. 2005 Dec. 15; 21 (24):4356-62; Pepe et al., Biometrics. 2006 March; 62(1):221-9; Wang et al.; Wang et al., J Proteomics Bioinform. 2012, 5:3; Liu A et al., Stat Med. 2005 Jan. 15; 24 (1):37-47. PubMed PMID: 15515132).

Examples of values for $a_i$ for two-marker combinations, depending on the marker combination, and based on the analysis of the serum samples obtained from the patients identified in Tables 3 and 4 of the instant application, are shown in Table 1. These $a_i$ values were those used to generate the ROC curves shown in FIGS. 6-10.

TABLE 1

Exemples of $a_1$ and $a_2$ coefficients maximizing AUC of ROC curve for two-marker combination

| Marker combination | $Z = a_1 \times Marker_1 + a_2 \times Marker_2$ |
|---|---|
| Ag_Mannan + Ab_Fba1 | Z = 0.499 × [Ag_Mannan*] + 2.324 × [Ab_Fba1*] |
| Ag_Mannan + Ab_Hwp1 | Z = 0.481 × [Ag_Mannan*] + 2.416 × [Ab_Hwp1*] |
| Ag_Mannan + Ab_Hsp90 | Z = 0.481 × [Ag_Mannan*] + 2.416 × [Ab_Hsp90*] |
| Ag_Mannan + Ab_Eno1 | Z = 0.453 × [Ag_Mannan*] + 1.916 × [Ab_Eno1*] |
| Ag_Mannan + Ab_Mp65 | Z = 0.486 × [Ag_Mannan*] + 2.261 × [Ab_Mp65*] |
| Ag_Mannan + Ab_Mannan | Z = 0.599 × [Ag_Mannan*] + 0.357 × [Ab_Mannan*] |

*levels of markers normalised by a log10 transformation.

The above values of $a_1$ and $a_2$ coefficients for two-marker combinations given in Table 1 are purely indicative as these values are liable to be modified with standardization of the methods. Furthermore, the $a_1$ and $a_2$ coefficients may depend on the measure units used for mannan antigen and antibody against *Candida* protein.

Once the values of the $a_i$ coefficients have been determined for a given marker combination, by standardisation on subject and control samples, a reference level of the virtual marker Z may be determined as a single value or a range of values, for instance as quantiles.

When the level of a *Candida* glycan and the level of an antibody directed against the *Candida* protein have been measured in a sample, or in at least two samples obtained at the same time from the same subject, a value of the virtual marker Z may be calculated for the test sample. If the calculated value for the virtual marker Z is higher than the reference level of the virtual marker Z, then the subject is developing or has developed invasive candidiasis.

Therefore, the invention also relates to a method which comprises the steps consisting of:
a) detecting the level of a *Candida* glycan in a blood, plasma or serum sample of the subject;
b) detecting the level of antibody directed against a *Candida* protein selected from the group consisting of fructose biphosphate aldolase (Fba1), enolase 1 (Eno1), heat shock protein 90 (Hsp90), hyphal wall protein (Hwp1), and mannoprotein 65 (Mp65) in the same blood, plasma or serum sample of the subject or in another blood, plasma or serum sample sequentially obtained from the same patient, essentially simultaneously; and
c) wherein a combined analysis of the level of said *Candida* glycan and the level of antibody directed against said *Candida* protein selected from the group consisting of Fba1, Eno1, Hsp90, Hwp1, and Mp65, is performed by calculating the level of a virtual marker $Z=\Sigma a_i \times [Marker_i]$ where [$Marker_i$] are individual levels of *Candida* glycan marker and of antibody directed against said *Candida* protein selected from the group consisting of Fba1, Eno1, Hsp90, Hwp1, and Mp65, and $a_i$ are coefficients which values are determined in order to maximize the Area Under the Curve (AUC) of the Relative Operating Characteristic (ROC) curve for the combination of $Marker_i$; and
d) wherein if the level of the virtual marker Z calculated in step c) is higher than a reference level of the virtual marker Z, then the subject is developing or has developed invasive candidiasis.

Method for Determining a Suitable Treatment Regimen

The high rates of mortality associated with invasive candidiasis (IC) are mainly due to the delay in identifying that a subject is affected with IC and initiating the appropriate antifungal treatment.

The invention further relates to a method for determining a treatment regimen in a subject, said method comprising:
a) diagnosing if the subject has invasive candidiasis by carrying out the method as described above, and
b) if the subject is diagnosed as having invasive candidiasis, determining an antifungal treatment for said subject.

The subject may be a subject suspected of having invasive candidiasis or at risk of invasive candidiasis. The subject may be in particular a subject having superficial infection of skin and/or mucosal membranes. The subject may also be for instance an immunocompromised subject bearing intravenous catheter.

An antifungal treatment may be for instance treatment with echinocandins which notably include Caspofungin (1-[(4R,5S)-5[(2-aminoethyl)amino]-N2-(10,12-dimethyl-1-oxotetradecyl)-4-hydroxy-L-ornithine]-5-[(3R)-3-hydroxy-L-ornithine]pneumocandin $B_0$), Micafungin and/or Anidulafungin (see for instance Patterson T F. Curr Infect Dis Rep 2006; 8:442-8). Echinocandins are synthetically modified lipopeptides which inhibit the synthesis of (1,3)-β-D-glucan. Another antifungal treatment may be for instance treatment with Enfumafungin and Enfumafungin derivatives such as described in the patent application published as US 20110224228. Amphotericin B and its lipidic formulations, or antifungal azole derivatives such as fluconazole, itraconazole, and Voriconazole (see for instance Pfaller et al. J Clin Microbiol 2006; 44:819-26; Mean et al. Crit Care 2008; 12:204) may also be used.

Combined administration of theses compounds, or combination with other active principles is possible.

The treatment is preferably administered as long as circulating mannan can be detected in the serum of the subject.

Kit for Diagnosing Invasive Candidiasis

The invention further relates to a kit comprising, or consisting of:
a) means for determining the presence or level of a *Candida* glycan as described above; and
b) means for determining the presence or level of antibody directed against a *Candida* protein selected from the group consisting of fructose bisphosphate aldolase (Fba1), enolase 1 (Eno1), heat shock protein 90 (Hsp90), hyphal wall protein (Hwp1), and mannoprotein 65 (Mp65), described above.

Means for determining the presence or level of a *Candida* glycan may be in particular means for determining the presence or level of *Candida* mannan, (1,3)-β-D-glucan or chitine. Such means may be in particular antibodies such as those described above (e.g. EBCA1 for mannan). Such means may also comprise a chromogenic substrate and enzyme(s) as are available in the Fungitell test (Associates of Cape Cod, Mass., USA).

Means for determining the presence or level of antibody directed against a *Candida* protein selected from the group consisting of Fba1, Eno1, Hsp90, hwp1 or Mp65 may comprise purified *Candida* protein, or epitopic fragments thereof, or a polypeptide comprising full length protein, epitopic fragments or variants thereof which have been recombinantly produced or chemical synthesized, as disclosed above.

The invention will be further illustrated in view of the following figures and examples.

FIGURES

FIGS. 1-5. Boxplot representation of diagnosis potential of anti-recombinant protein-antibody [RP-Ab; respectively anti-Fba1 Ab (FIG. 1); anti-Hwp1 Ab (FIG. 2); anti-Hsp90 Ab (FIG. 3); anti-Eno1 Ab (FIG. 4); anti-Mp65 Ab (FIG. 5)] or anti-mannan antibodies associated with mannanemia. Boxplot representation is a convenient way of graphically depicting groups of numerical data through their five-number summaries (the smallest observation, lower quartile (Q1), median (Q2), upper quartile (Q3), and largest observation). Boxplots can be useful to display differences between populations without making any assumptions of the underlying statistical distribution. CTRL represents controls and IC represents invasive candidiasis patients.

FIGS. 6-10. ROC curves of combinations of RP-Ab [respectively anti-Fba1 Ab (FIG. 6); anti-Hwp1 Ab (FIG. 7); anti-Hsp90 Ab (FIG. 8); anti-Eno1 Ab (FIG. 9); anti-Mp65 Ab (FIG. 10)] with mannanemia. The actual diagnosis (mannan Antibody and mannan Antigen) test was represented with dotted lines and association of RP-Ab and mannanemia was represented with black line.

EXAMPLES

Example 1

Recombinant Protein Production in *E. coli*

1) Strains and Plasmids

*Candida albicans* SC5314 was used as fungal DNA source to generate the different recombinant proteins. *Escherichia coli* strain DE3 was transformed to produce the recombinant proteins while the strain DH5α was used to amplify the plasmids.

2) Cloning

Six recombinant proteins were expressed in *E. coli* as described previously (Fradin et al., Infect Immun (2008), 76: 4509-4517): N-terminal fragment of Hwp1 (amino acids 27 to 203), Eno1 (full length), Mp65 without its peptide signal (amino acids 1 to 22), Fba1 (full length), Sod5 without its peptide signal (amino acids 1 to 22) and its C-terminal GPI consensus sequence (last 24 terminal amino acids) and Hsp90 (full length).

Six sets of primers (Table 2 below) were designed to clone the different genes or truncated genes. PCR amplified fragments with high fidelity Expand Taq polymerase (Roche) were directly cloned in pEXP5-NT/TOPO plasmid.

TABLE 2

Set of primers used for gene cloning

| Recombinant proteins | Primers set |
|---|---|
| N-term Hwp1 | 5'CAAGGTGAAACAGAGGAAGCT3' (SEQ ID NO: 17) and<br>5'TCAAGCAGGAATGTTTGGAGTAGT3' (SEQ ID NO: 18) |
| Eno1 | 5'ATGTCTTACGCCACTAAAATCCACGC3' (SEQ ID NO: 19) and<br>5'TTACAATTGAGAAGCCTTTTGGAAATCTTTAC3' (SEQ ID NO: 20) |
| Mp65 | 5'GCTCATCAACATCATCAACAT3' (SEQ ID NO: 21) and<br>5'TTAGTTAGAGTAAATACCCCAGTA3' (SEQ ID NO :22) |
| Fba1 | 5'ATGGCTCCTCCAGCAGTTTTA3' (SEQ ID NO: 23) and<br>5'TTACAATTGTCCTTTGGTGTG3' (SEQ ID NO: 24) |
| Sod5 | 5'GATGCACCAATCTCAACTGAC3' (SEQ ID NO: 25) and<br>3'TTAACCTTGAGGAGCAGTAGAAGC3' (SEQ ID NO: 26) |
| Hsp90 | 5'ATGGCTGACGCAAAAGTTGAA3' (SEQ ID NO: 27) and<br>5'TTAATCAACTTCTTCCATAGC3' (SEQ ID NO: 28) |

Example 2

Evaluation of Diagnosis Potential of Anti-Recombinant Protein-Antibodies or Anti-Mannan Antibodies Associated with Mannanemia 1) Materials and Methods Patients Between January 2005 and December 2007, 157 serum samples were retrospectively collected in different clinical departments of Lille University Hospital (LUH), from 53 patients (24 females and 29 males [mean age, 56.78+/−23.71 years]) with proven *Candida albicans* candidiasis. The average number of samples per patient in this group was 2.68+/−2.13 (Table 3).

TABLE 3

Clinical features of patients with systemic *Candida albicans* infection. Patients were classified according to clinical wards

| Patient | Sex[a] | Age (yr) | Hospital ward | No. Of sera | Date of serum sampling in relation to blood culture (days) | *Candida* species |
|---|---|---|---|---|---|---|
| 1 | F | 34 | Burn unit | 7 | −10, −3, 0, 4, 13, 18, 22 | *Candida albicans* |
| 2 | M | 43 | Burn unit | 4 | −16, −9, 12, 27 | *Candida albicans* |
| 3 | M | 54 | Burn unit | 3 | −6, −4, 10 | *Candida albicans* |
| 4 | F | 54 | Burn unit | 4 | −10, −3, 4, 11 | *Candida albicans* |

TABLE 3-continued

Clinical features of patients with systemic *Candida albicans* infection. Patients were classified according to clinical wards

| Patient | Sex[a] | Age (yr) | Hospital ward | No. Of sera | Date of serum sampling in relation to blood culture (days) | Candida species |
|---|---|---|---|---|---|---|
| 5 | F | 59 | Burn unit | 1 | 17 | *Candida albicans* |
| 6 | M | 68 | Burn unit | 4 | −10, −3, 4, 18 | *Candida albicans* |
| 7 | F | 75 | Burn unit | 2 | 7, 14 | *Candida albicans* |
| 8 | M | 81 | Cardiology | 1 | 6 | *Candida albicans* |
| 9 | F | 31 | Gastroenterology | 1 | 0 | *Candida albicans* |
| 10 | M | 53 | Gastroenterology | 1 | 2 | *Candida albicans* |
| 11 | M | 59 | Gastroenterology | 3 | −6, −2, 6 | *Candida albicans* |
| 12 | M | 78 | Heat surgery | 1 | 1 | *Candida albicans* |
| 13 | F | 46 | Clinical hematology | 8 | −8, −5, 1, 5, 5, 16, 22, 27 | *Candida albicans* |
| 14 | F | 62 | Clinical hematology | 7 | −3, 4, 12, 14, 20, 27, 29 | *Candida albicans* |
| 15 | M | 70 | Clinical hematology | 6 | 3, 10, 13, 17, 19, 24 | *Candida albicans* |
| 16 | F | 86 | Infectious diseases | 3 | 1, 7, 14 | *Candida albicans* |
| 17 | M | 10 | Intensive care unit | 2 | 3, 23 | *Candida albicans* |
| 18 | F | 14 | Intensive care unit | 1 | 4 | *Candida albicans* |
| 19 | M | 32 | Intensive care unit | 2 | 14, 30 | *Candida albicans* |
| 20 | M | 35 | Intensive care unit | 1 | −1 | *Candida albicans* |
| 21 | F | 36 | Intensive care unit | 2 | 3, 10 | *Candida albicans* |
| 22 | M | 46 | Intensive care unit | 2 | −2, 5 | *Candida albicans* |
| 23 | M | 47 | Intensive care unit | 6 | −3, 4, 13, 20, 27, 28 | *Candida albicans* |
| 24 | M | 49 | Intensive care unit | 2 | −6, −2 | *Candida albicans* |
| 25 | F | 50 | Intensive care unit | 1 | 0 | *Candida albicans* |
| 26 | M | 57 | Intensive care unit | 6 | −8, −2, 5, 12, 20, 27 | *Candida albicans* |
| 27 | F | 59 | Intensive care unit | 2 | 3, 4 | *Candida albicans* |
| 28 | M | 60 | Intensive care unit | 5 | −10, −3, 4, 11, 25 | *Candida albicans* |
| 29 | F | 62 | Intensive care unit | 4 | −12, −5, 2, 9 | *Candida albicans* |
| 30 | M | 64 | Intensive care unit | 2 | 2, 9 | *Candida albicans* |
| 31 | M | 66 | Intensive care unit | 5 | 2, 6, 8, 12, 13 | *Candida albicans* |
| 32 | M | 72 | Intensive care unit | 4 | −5, 2, 6, 9 | *Candida albicans* |
| 33 | F | 75 | Intensive care unit | 1 | 3 | *Candida albicans* |
| 34 | F | 76 | Intensive care unit | 9 | 4, 7, 11, 14, 17, 22, 25, 27, 28 | *Candida albicans* |
| 35 | F | 79 | Intensive care unit | 9 | −1, 3, 4, 5, 6, 13, 14, 20, 27 | *Candida albicans* |
| 36 | F | 82 | Intensive care unit | 1 | 5 | *Candida albicans* |
| 37 | F | 87 | Intensive care unit | 4 | 2, 7, 22, 29 | *Candida albicans* |
| 38 | M | 89 | Intensive care unit | 2 | −7, −1 | *Candida albicans* |
| 39 | M | 48 | intensive surgical care unit | 1 | 2 | *Candida albicans* |
| 40 | M | 72 | intensive surgical care unit | 1 | 0 | *Candida albicans* |
| 41 | M | 72 | intensive surgical care unit | 3 | −3, 4, 16 | *Candida albicans* |
| 42 | F | 73 | intensive surgical care unit | 2 | −5, 25 | *Candida albicans* |
| 43 | M | 73 | intensive surgical care unit | 1 | 11 | *Candida albicans* |
| 44 | M | 78 | intensive surgical care unit | 1 | 2 | *Candida albicans* |
| 45 | F | 83 | intensive surgical care unit | 2 | −9, 19 | *Candida albicans* |
| 46 | M | 15 | Oncology | 2 | −5, 1 | *Candida albicans* |
| 47 | M | 6 | Paediatrics | 6 | 15, 17, 18, 19, 24, 26 | *Candida albicans* |
| 48 | F | 14 | Paediatrics | 1 | −1 | *Candida albicans* |
| 49 | F | 17 | Paediatrics | 3 | −15, −8, 6 | *Candida albicans* |
| 50 | M | 53 | Pneumology | 2 | −11, −10 | *Candida albicans* |
| 51 | F | 80 | Pneumology | 1 | 4 | *Candida albicans* |
| 52 | M | 64 | Transplantation | 1 | −1 | *Candida albicans* |
| 53 | F | 49 | Traumatology | 1 | 0 | *Candida albicans* |

[a]M, male; F, female

A second group of 142 serum samples was also collected in different departments of LUH from 40 patients (10 females and 30 males [mean age, 58.00+/−21.97]) with proven invasive candidiasis determined by non-albicans yeast species (Table 4). The average number of samples per patient in this group was 3.59+/−2.66. This group contains 7 different yeast species: *Candida parapsilosis* (17 patients; 49 sera), *Candida kruseï* (3 patients; 10 sera), *Candida tropicalis* (5 patients; 20 sera), *Candida glabrata* (12 patients; 40 sera), *Geotrichum capitatum* (1 patient; 12 sera), *Candida norvegiensis* (1 patient; 3 sera) and *Candida lusitaniae* (1 patient; 8 sera).

TABLE 4

Clinical features of patients with systemic *Candida* infection. Patients were classified according to yeast species involved in IC and to clinical wards

| Patient | Sex[a] | Age (yr) | Hospital ward | No. of sera | Date of serum sampling in relation to blood culture (days) | Candida species |
|---|---|---|---|---|---|---|
| 54 | M | 21 | Burn unit | 2 | −1, 12 | *Candida parapsilosis* |
| 55 | M | 43 | Burn unit | 4 | −6, 0, 7, 21 | *Candida parapsilosis* |
| 56 | F | 82 | Clinical hematology | 2 | 2, 7 | *Candida parapsilosis* |
| 57 | M | 24 | Intensive care unit | 4 | −11, −6, 0, 1 | *Candida parapsilosis* |

TABLE 4-continued

Clinical features of patients with systemic *Candida* infection. Patients were classified according to yeast species involved in IC and to clinical wards

| Patient | Sex[a] | Age (yr) | Hospital ward | No. of sera | Date of serum sampling in relation to blood culture (days) | *Candida* species |
|---|---|---|---|---|---|---|
| 58 | M | 51 | Intensive care unit | 1 | 25 | *Candida parapsilosis* |
| 59 | M | 54 | Intensive care unit | 5 | −10, −3, 4, 10, 18 | *Candida parapsilosis* |
| 60 | M | 65 | Intensive care unit | 1 | −11 | *Candida parapsilosis* |
| 61 | M | 67 | Intensive care unit | 4 | −11, −4, 3, 17 | *Candida parapsilosis* |
| 62 | F | 75 | Intensive care unit | 1 | 23 | *Candida parapsilosis* |
| 63 | M | 76 | Intensive care unit | 5 | −15, −12, 2, 6, 9 | *Candida parapsilosis* |
| 64 | M | 78 | Intensive care unit | 3 | −8, −3, 4 | *Candida parapsilosis* |
| 65 | M | 87 | Intensive care unit | 7 | −14, −7, 0, 7, 14, 21, 22 | *Candida parapsilosis* |
| 66 | F | 87 | Intensive care unit | 2 | −5, 8 | *Candida parapsilosis* |
| 67 | M | 65 | Intensive surgical care unit | 2 | 0, 1 | *Candida parapsilosis* |
| 68 | M | 57 | Intensive surgical care unit | 4 | −5, 1, 9, 23 | *Candida parapsilosis* |
| 69 | M | 90 | Intensive surgical care unit | 1 | 3 | *Candida parapsilosis* |
| 70 | F | 10 | Paediatrics | 1 | 3 | *Candida parapsilosis* |
| 71 | M | 47 | Clinical hematology | 3 | −11, −4, 3 | *Candida krusei* |
| 72 | M | 68 | Clinical hematology | 6 | −9, −7, −1, 4, 12, 19 | *Candida krusei* |
| 73 | M | 75 | Oncology | 1 | 4 | *Candida krusei* |
| 74 | M | 39 | Burn unit | 5 | −15, −8, 10, 13, 28 | *Candida tropicalis* |
| 75 | M | 51 | Clinical hematology | 1 | 3 | *Candida tropicalis* |
| 76 | F | 62 | Clinical hematology | 10 | −15, −6, −2, −1, 0, 1, 3, 5, 7, 12 | *Candida tropicalis* |
| 77 | M | 8 | Intensive care unit | 3 | 1, 8, 18 | *Candida tropicalis* |
| 78 | M | 67 | Oncology | 1 | −5 | *Candida tropicalis* |
| 79 | M | 24 | Hyperbare | 2 | −2, 5 | *Candida glabrata* |
| 80 | M | 31 | Intensive care unit | 1 | 3 | *Candida glabrata* |
| 81 | M | 57 | Intensive care unit | 5 | 0, 6, 13, 20, 27 | *Candida glabrata* |
| 82 | M | 63 | Intensive care unit | 4 | −10, 2, 10, 11 | *Candida glabrata* |
| 83 | M | 63 | Intensive care unit | 8 | −5, −4, −1, 0, 1, 3, 7, 12 | *Candida glabrata* |
| 84 | F | 69 | Intensive care unit | 1 | 14 | *Candida glabrata* |
| 85 | F | 76 | Intensive care unit | 5 | −9, −5, 2, 9, 16 | *Candida glabrata* |
| 86 | F | 87 | Intensive care unit | 3 | −7, 7, 12 | *Candida glabrata* |
| 87 | F | 24 | Intensive surgical care unit | 5 | −11, −7, −5, 0, 10 | *Candida glabrata* |
| 88 | M | 71 | Intense surgical care unit | 2 | 1, 15 | *Candida glabrata* |
| 89 | M | 85 | intensive surgical care unit | 3 | 2, 4, 11 | *Candida glabrata* |
| 90 | F | 60 | Oncology | 1 | 8 | *Candida glabrata* |
| 91 | M | 64 | Clinical hematology | 12 | −15, −11, −9, −6, −3, −1, 1, 4, 6, 11, 13, 15 | *Geotrichum capitatum* |
| 92 | M | 45 | Clinical hematology | 3 | 1, 7, 12 | *Candida norvegensis* |
| 93 | M | 76 | Clinical hematology | 8 | −10, −3, −1, 1, 4, 6, 8, 11 | *Candida lusitaniae* |

[a] M, male; F, female

The following criteria were applied as retrospective selection rules when the laboratory and clinical files were examined: (i) positive blood culture from *Candida* species; (ii) availability of serum samples obtained within a range of 3 weeks before and 1 month after positive cultures, (iii) the presence of risk factors (cancer and chemotherapy, abdominal surgery, AIDS, major health problems requiring hospitalization in intensive care units -ICUs-, and use of broad-spectrum antibiotics, indwelling intravascular catheters, and hyperalimentation; and (iv) the presence of an infectious syndrome (namely, fever) that did not respond to antibacterial therapy but that did respond to antifungal therapy. In order to evaluate performances of biomarkers for the early diagnosis of IC, selection of serum samples was restricted to the period ranging from 2 weeks before to 1 month after the date of isolation of yeast species from blood culture. After blood sampling blood samples were centrifuged and serum aliquots were stored at −80° C. until required.

Control Group.

Two groups of control sera were included in this study:
(i) Group 1 comprised 90 serum specimens from 90 hospitalized patients (32 females and 58 males; mean age, 64+/−15.5 years) without evidence of invasive candidiasis. This group of patients was enrolled in a prospective study conducted in an ICU of LUH for 6 months. The study was designed for the assessment of risk factors for nosocomial candidiasis. These patients were under clinical and mycological survey for periods ranging from 1 to 74 days (mean, 12 days). Samples of blood, oral swabs, urine, and stools were collected biweekly. Among them 90 patients, 71 were colonized by yeast species with evaluation of number of colonized body sites: 1 site (16.9%), 2 sites (26.8%), 3 sites (26.8%), 4 sites (25.3%) and 5 sites (4.2%).
(ii) Group 2 consisted of 80 serum samples from healthy blood donors.

EIA Detection of Anti-*C. albicans* Mannan Antibodies in Human Sera.

Antibodies to *Candida albicans* mannan were detected using the Platelia *Candida* antibody (Ab) Plus test (Bio-Rad Laboratories, Marnes La-Coquette, France) according to manufacturer's instructions. Briefly, Enzyme ImmunoAssay (EIA) was performed with BEP III automate (Behring Laboratories, Paris, France). For individual sera, 100 μl of serum diluted 1/400 was applied to each well, and the plate was incubated for 1 h at 37° C. After washing, 100 μl of horseradish peroxidase-conjugated anti-human immunoglobulins was then added, and the plates were incubated for 1 h at 37° C. After intensive washing, the reaction was revealed by 30 min of incubation in darkness with 200 μl of tetramethylbenzidine solution. The absorbance at a λ of 450/620 nm was measured. The results were reported in arbitrary units (AU) in relation to the results on the standard curve.

Detection of Mannanemia.

Circulating mannan was detected using the Platelia *Candida* antigen Plus (Ag) test (Bio-Rad Laboratories, Marnes- La-Coquette, France) as described previously (Sendid et al., J Med Microbiol. 2002 May; 51(5):433-42). Briefly, microtiter plates were sensitized in an industrial setting with monoclonal antibody (monoclonal antibody EBCA1 of Platelia Candida antigen Plus (Ag) test). 300 µl of patient sera was denatured with 100 µl of EDTA treatment solution, and the mixture was boiled for 3 min and centrifuged at 10,000 g for 10 min. 50 µl of supernatant, obtained from patient serum and treated as described above, was mixed in a plate well with 50 µl of horseradish peroxidase-conjugated EBCA1. After incubation for 90 min at 37° C., the plates were washed intensively and the reaction was revealed by 30 min of incubation in darkness with 200 µl of tetramethylbenzidine solution. The optical density was read at a $\lambda$ of 450/620 nm on a PR2100 reader (Sanofi Pasteur Diagnostics). Reactions were performed in duplicate. Each experiment included a calibration curve for a pool of normal human sera supplemented with concentrations of mannan of 0.1 to 27 ng/ml.

EIA Detection of Anti-C. albicans Recombinant Proteins Antibodies in Human Sera

Recombinant proteins were coated on ELISA plates (NUNC IMMUNO-MODULE 468680) at a concentration of 2 µg/ml for Mp65 and Eno1, and at a concentration of 4 µg/ml for Fba1, Hwp1 and Hsp90 produced in *Escherichia coli*, with carbonate solution pH 9.5+/−0.2 filtered 0.22 µm for all antigens. These preparations were incubated at room temperature overnight.

After coating, the wells were blocked by 100 µl of Bovine Serum Albumin/Saccharose solution pH 7.2+/−0.2 filtered 0.22 µm, emptied and filled with 200 µl of the same solution. Plates were then frozen at −20° C. Protocols for antigens coating, preparation of diluent solutions, dilution of patient sera, and conjugate solutions were based on preliminary experiments performed with a pool of sera from IC patients known to display high titers of anti-Candida antibodies.

Patient sera were diluted 1/100 in Tris saline buffer and BSA pH 7.6 and were incubated for 1 h at 37° C. on coated plate in dry incubator, 3 times washed with 800 µl of Tris saline buffer and Tween 20 (0.1%) and proclin (0.07%), incubated 1 h at 37° C. with a secondary anti-total immunoglobulin antibody conjugated to peroxidase (Bio-Rad, Marnes La Coquette, France), washed 3 times as previously described and incubated 30 minutes with 200 µl of tetramethyl benzidine (TMB) and stored at room temperature in dark. The reaction was stopped by the addition of 100 µl of stopping solution containing 2M $H_2SO_4$ and ODs were measured at 450/620 nm. In parallel, all sera were tested at the same time with the home-made EIA tests involving recombinant proteins, the Platelia™ Candida Ab Plus and the Platelia™ Candida Ag.

Statistical Analysis

Statistical analysis was performed in collaboration with SysDIAG: Systèmes Complexes pour le Diagnostic (UMR3145 CNRS/Bio-Rad, Montpellier, France). All statistics and figures were computed with the "R/Bioconductor" statistical open source software (Ge et al. Test 2003; 12:1-77; Gentleman et al. Genome Biol 2004; 5:R80) or SAS software v9.2 (SAS institute Inc). A differential analysis was carried out with the non-parametric Wilcoxon rank sum test and the Welch test. With the multiple testing methodologies, it is important to adjust the p-value of each marker to control the False Discovery Rate (FDR). The Benjamini and Hochberg (BH) procedure (Benjamini et al. Behav Brain Res 2001; 125:279-84) was applied on all statistical tests with the "multitest package" and an adjusted p-value below 0.05 was considered as statistically significant. A logarithmic transformation (log 10) was applied on the biomarker expression levels to ensure the data normality. All data distributions are illustrated as medians and boxplots for each biomarker. A Pearson test correlation was applied to identify biomarker correlation for all patient groups.

The marker diagnostic performance could be characterised by sensitivity, which represents its ability to detect the IC population, and specificity which represents its ability to detect the control population.

The results of the evaluation of a diagnostic test can be summarised in a 2×2 contingency table comparing these two well-defined populations. By fixing a cut-off the two populations could be classified into categories according to the results of the test, categorised as either positive or negative. Given a particular marker, we can identify a number of subjects with a positive test result among the "cases" population (the "True Positive": TP) and b subjects with a positive test result among the "controls" population (the "True Negative": TN). In the same fashion, c subjects with a negative test result among the cases (the "False Positive": FP) and d subjects with a negative test result among the controls (the "False Negative": FN) are observed. Sensitivity is defined as TP/(TP+FN); which is herein referred to as the "true positive rate". Specificity is defined as TN/(TN+FP); which is herein referred to as the "true negative rate".

The accuracy of each marker and its discriminatory power was evaluated using a Receiving Operating Characteristics (ROC) analysis. ROC curves are the graphical visualization of the reciprocal relation between the sensitivity (Se) and the specificity (Sp) of a test for various values.

In addition, all markers were combined with Mannan antigen (Ag) to evaluate the potential increase in sensibility and specificity using several approaches as mROC program (Kramar et al. Computer Methods and Programs in Biomedicine 2001; 66:199-207), logistic regression (Kleinbaum, D. G., Kupper, L. L., Muller, K. E. (1988) Applied Regression Analysis and other Multivariate Methods. Duxbury Press, Belmont, Calif.) and with two supervised learning algorithms, CART (Breiman L. Classification and regression trees. Wadsworth International Group, 1984.) and wKNN (Hechenbichler K, Schliep K. Weighted k-Nearest-Neighbor Techniques and Ordinal Classification. Volume 399, 2004).

mROC is a program developed by Kramar et al. (Comput Methods Programs Biomed, 2001, 66:199-207) which is dedicated to identify the linear combination which maximizes the AUC (Area Under the Curve) of ROC curves. The use of this program was described for instance in Staack et al. BMC Urol 2006; 6:19. This program implements an algorithm for maximising rank correlation estimation which is also an estimate for the area under the ROC curve (Su and Liu. Journal of the American Statistical Association 1993; 88:1350-1355; Wang, Computational Statistics and Data Analysis 2007; 51:2803-2812). The equation for the respective combination is provided and can be used as a new virtual marker Z, as follows:

$$Z = a \times \mathrm{Marker}_1 + b \times \mathrm{Marker}_2 + c \times \mathrm{Marker}_3,$$

where a, b, c are calculated coefficients and $\mathrm{Marker}_{1,2,3}$ are individual level of markers.

A logistic regression model was also applied for univariate and multivariate analysis to estimate the relative risk of IC at different biomarkers values. We analyzed biomarkers as both continuous (data not shown) and categorical (using the quartile values as cutpoints) variables. In the last cases, the odds ratio (OR) and their 95% confidence interval are computed.

A CART (Classification And Regression Trees) approach was also applied to assess (biomarker+Mannan Ag) combinations. This decision tree approach allows to produce a set of classification rules, represented by a hierarchical graph easily understandable for the user. At each node of the tree, a decision is made. By convention, the left branch corresponds to a positive response to the question of interest and the right branch corresponds to a negative response to the question of interest. The classification procedure can then be translated as a set of rules 'IF-THEN'.

A wKNN (weighted k-nearest neighbours) approach was applied as previously to assess (biomarker+Mannan Ag) combinations. The wKNN algorithm is one of the variations of KNN method which uses the K nearest neighbours, regardless of their classes, but then uses weighted votes from each sample rather than a simple majority or plurality voting rule. Given a patient x, each of the K samples provides a weighted vote that is usually equal to some decreasing function of its distance from the unknown sample x. These weighted votes are then summed for each neighbour, and the class with the largest total vote is attributed to x.

CART and wKNN are supervised learning methods. These methods require the use of a training set used to construct the model and a test set to validate it. So, we have shared our data set: ⅔ of the dataset are used for the learning phase and ⅓ are used for the validation phase. This sharing has been randomized and respect the initial proportion of the various statutes in each sample. To estimate the errors prediction of these two classifiers, we used the 10-fold cross-validation method, repeated 10 times in order to avoid overfitting problems. For these approaches, we used the "ipred package", the "rpart package" and the "kknn package" of the R software.

Hierarchical Ascendant Clustering Analysis (HAC) is a method of cluster analysis, based on a pairwise distance matrix, which builds a hierarchy of clusters with sequentially agglomerative and divisive approaches. We have used this method to organize the map and to group the sample according to the nearest level of biomarker intensity. For this analysis, raw data were mean-centred and Pearson correlation matrix and average linkage were chosen as parameters.

2) Results

Standardization of Tests.

For each experiment, 3 serum controls were used. Negative control collected from healthy subject and 2 positive sera consisted of 1 pool of sera with known reactivity against *Candida albicans* mannan and one serum collected from patient belonging to IC group selected from previous series of experiments. All these controls allowed us to reduce inter-experiments variations.

A study of diagnosis potential of different recombinant proteins was performed by comparison of medians. When serological data were analyzed, antibodies against Fba1 (Fba1 Ab), Hwp1 (Hwp1 Ab), Hsp90 (Hsp90 Ab), Eno1 (Eno1 Ab) and Mp65 (Mp65 Ab) are the best biomarkers to discriminate IC patients from controls, however humoral response against Sod5 was less discriminant for both groups.

Figure 2:
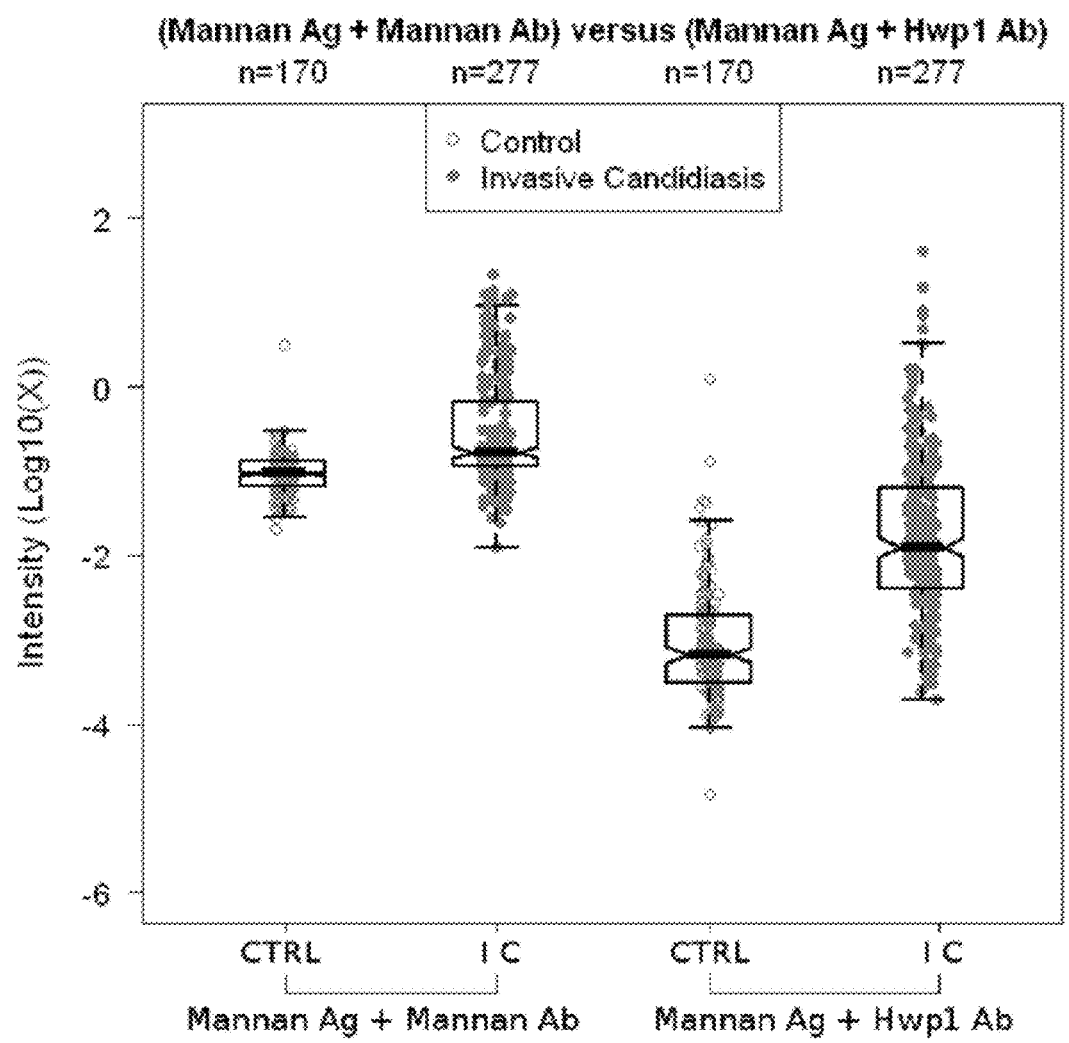
Figure 3:
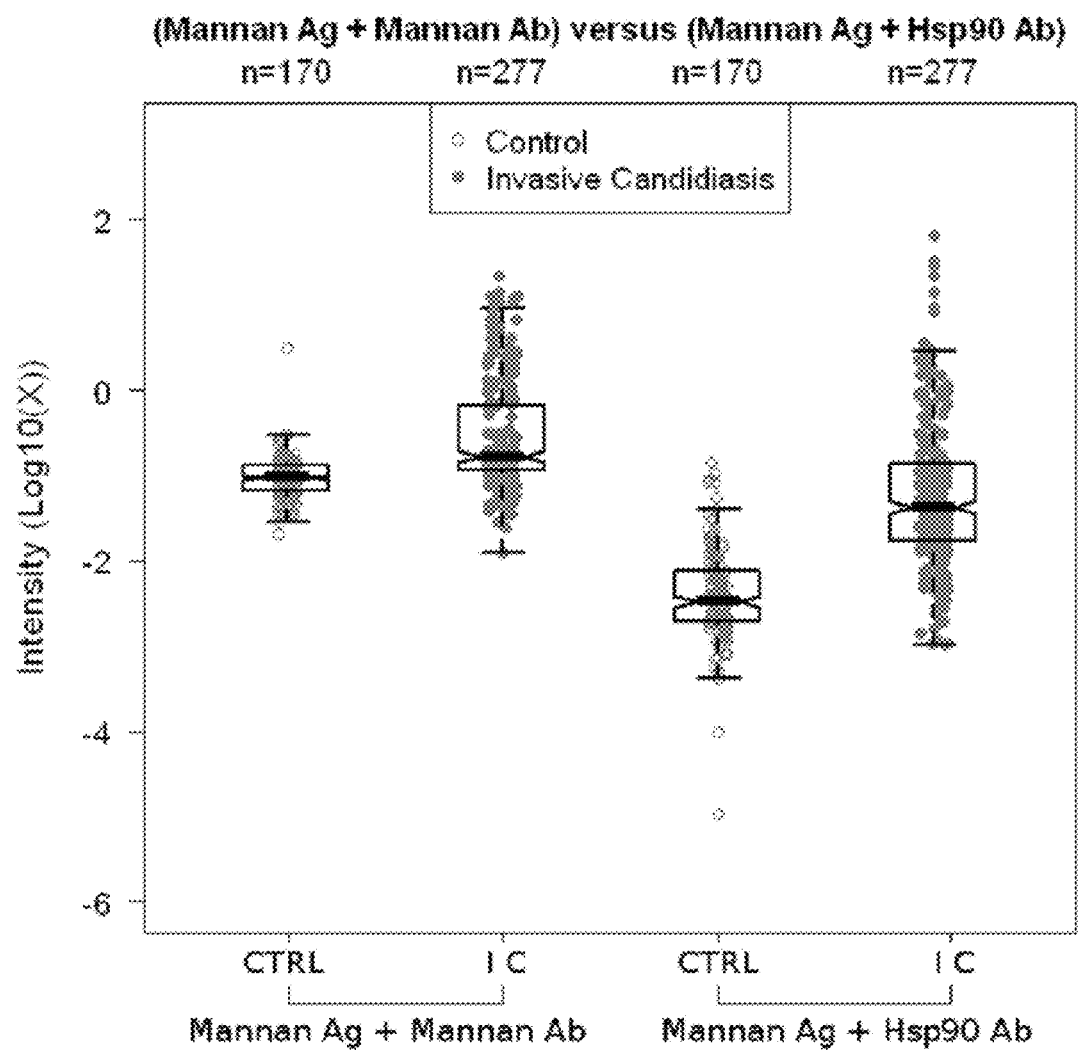
Figure 4:
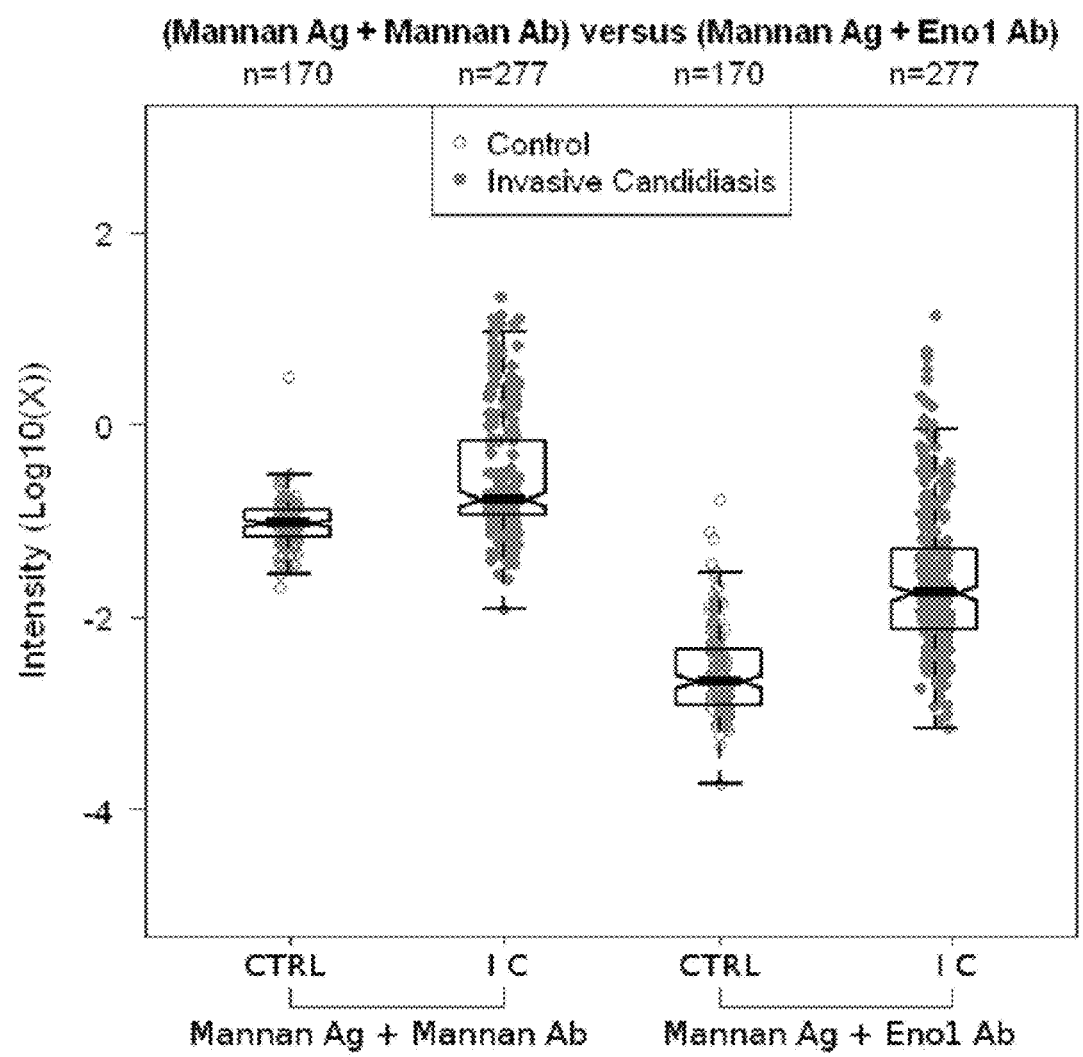
Figure 5:
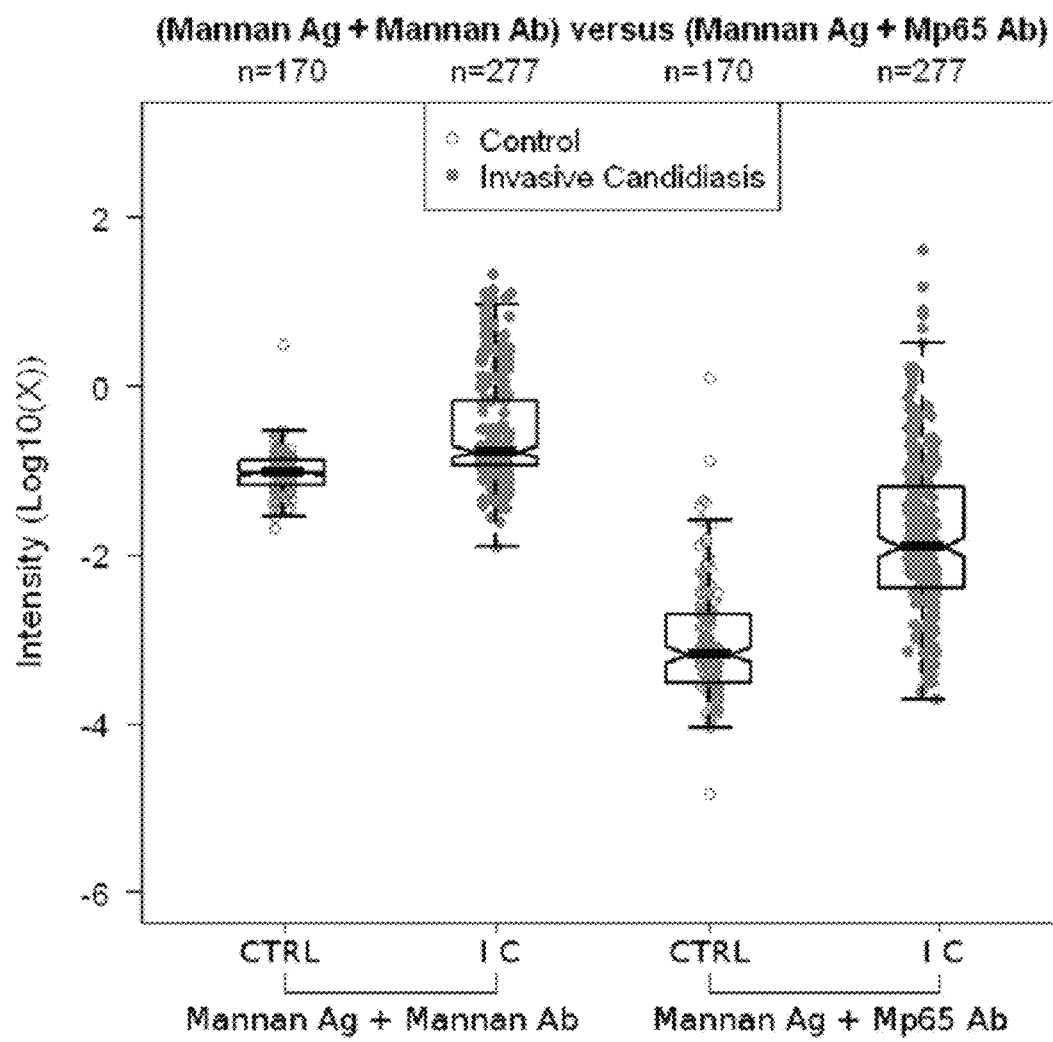
Figure 6:
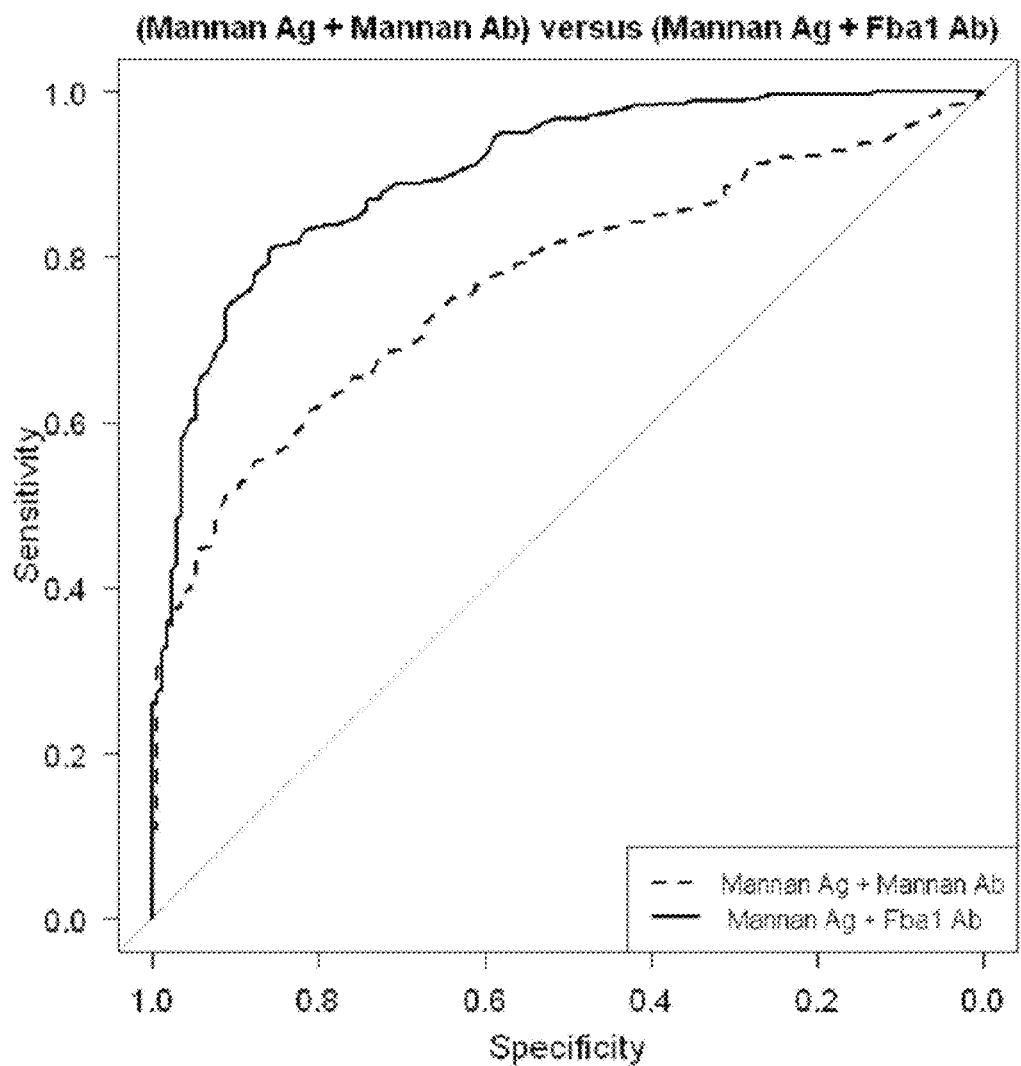
Figure 7:
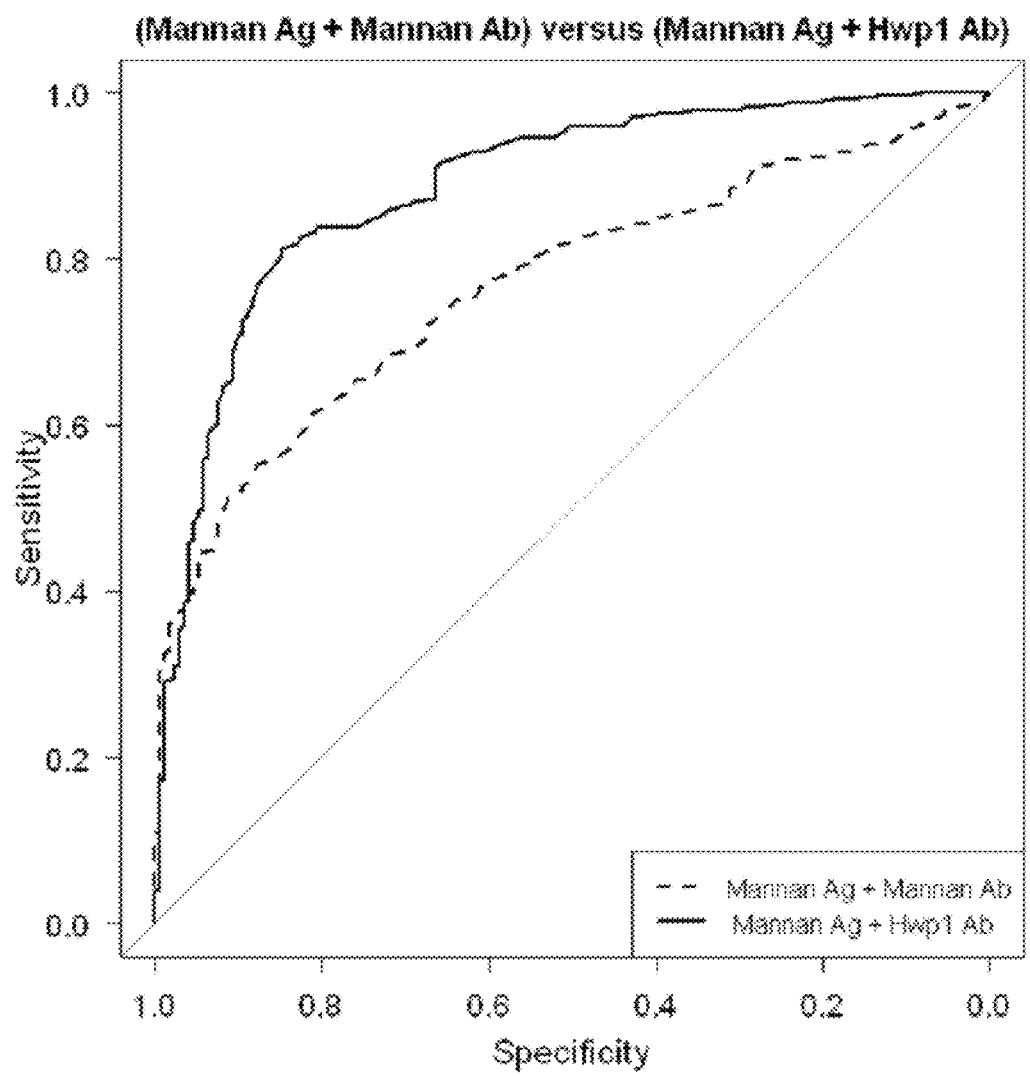
Figure 8:
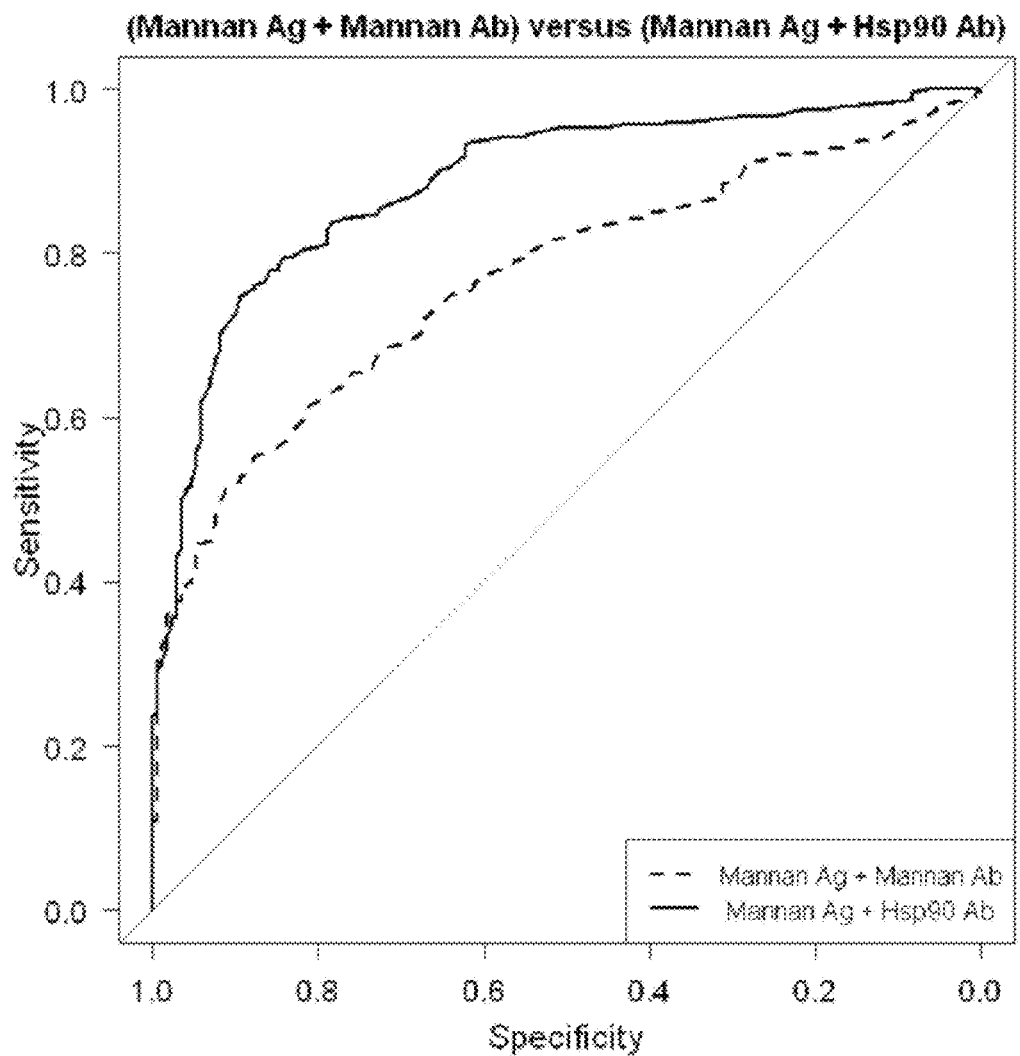
Figure 9:
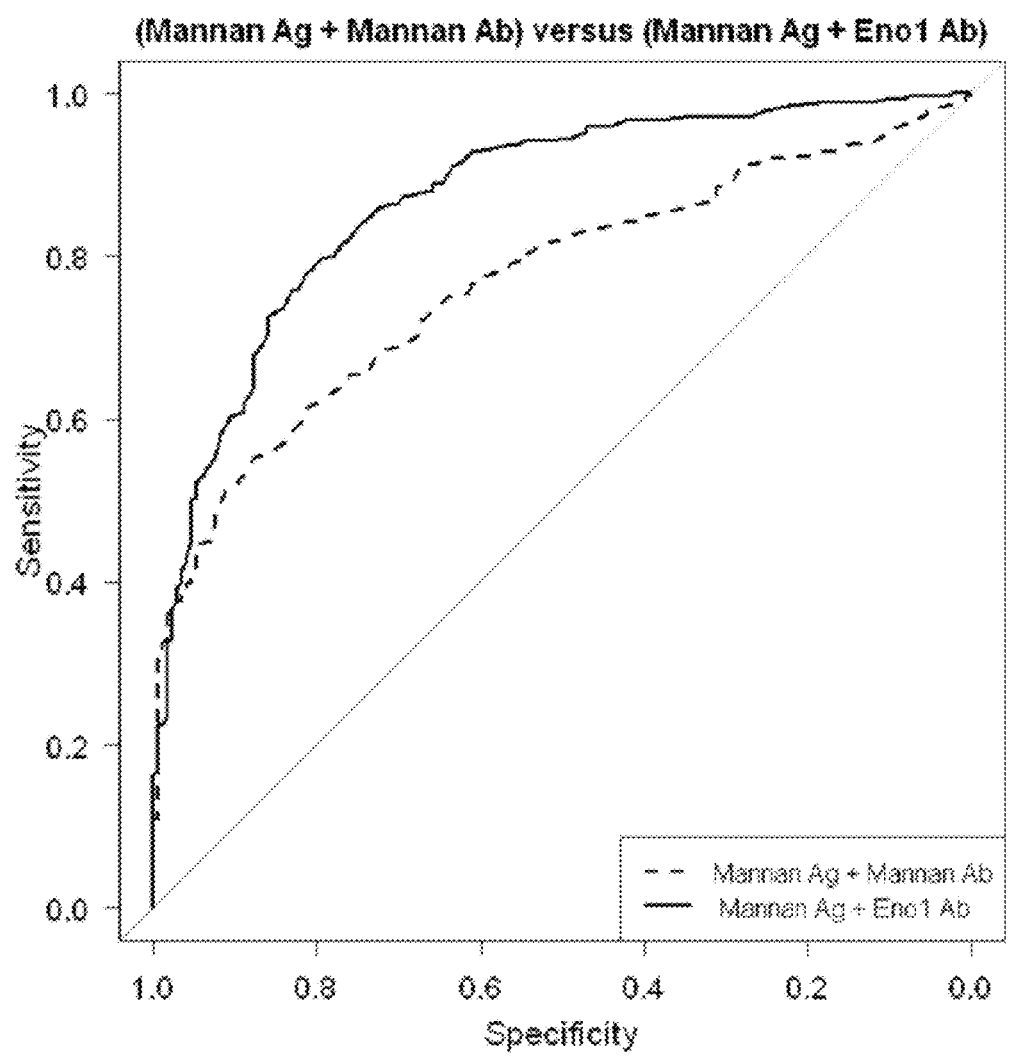
Figure 10:
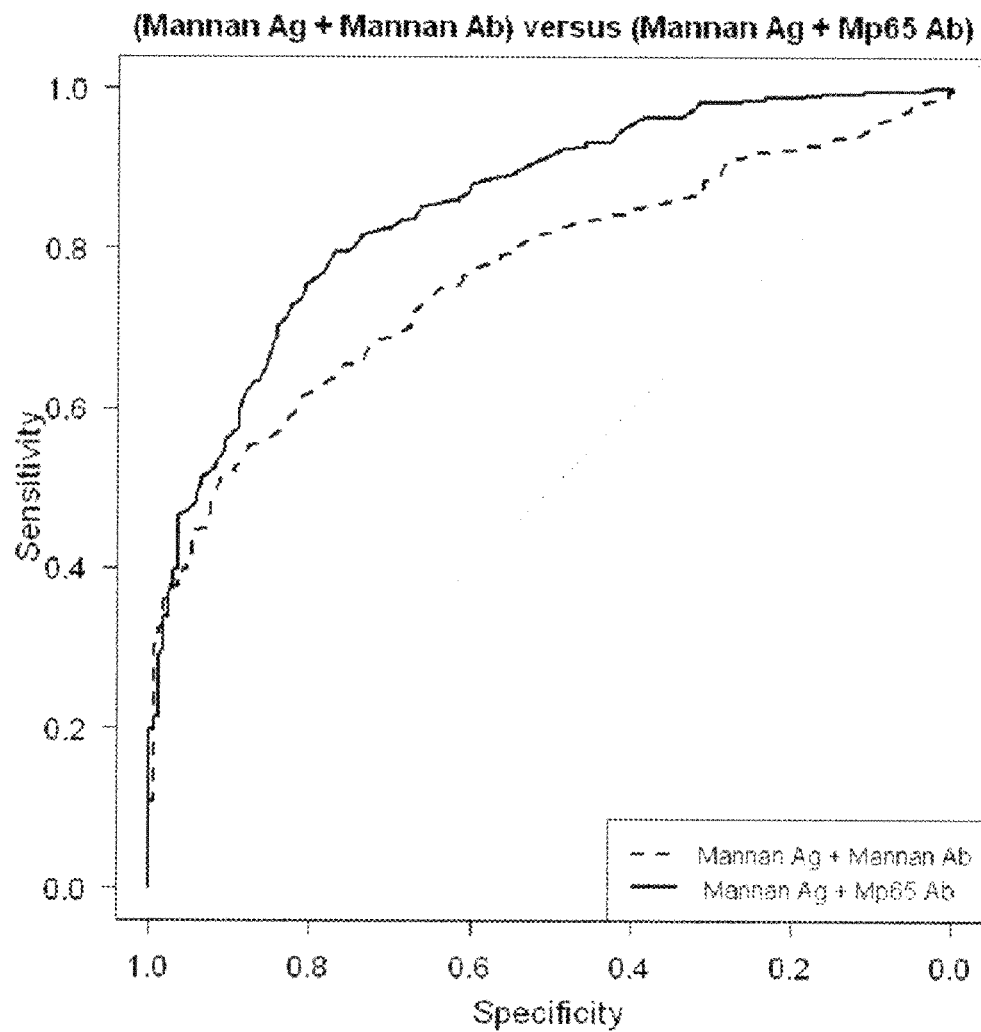

Comparison of Serological Reactivity Against a Panel of Antigens within IC and Control Groups Using all group of patients (IC versus controls), boxplots were performed for each combination of mannanemia test and EIA tests involving recombinant proteins (FIGS. 1-5). When antibody response against each recombinant protein associated to mannanemia test was compared to mannanemia and anti-mannan antibody tests, significant differences were observed for Fba1 ($p<0.0001$; FIG. 1), Hwp1 ($p<0.0001$; FIG. 2), Hsp90 ($p<0.0001$; FIG. 3), Eno1 ($p<0.0001$; FIG. 4) and Mp65 ($p<0.0001$; FIG. 5).

Analysis of Discriminatory Potential of Each RP-Ab/Mannanemia Combination in Compared with the Mannanemia and Anti-Mannan Antibody Association Combinations of more than 2 markers were tested however none have significantly improved the results obtained combining mannanemia and one of anti-protein recombinant antibodies.

ROC curves show the improvement of IC diagnostic with combination of RP-Ab and mannan antigen compared with combination of mannan antigen and anti-mannan antibody (FIGS. 6-10).

Comparison of Sensitivity and Specificity of Mannanemia and RP-Ab Combined Analysis.

Retrospective analysis of the cohort allowed sensitivity and a specificity of 26.6% and 99.4% respectively for mannanemia alone when combination of Platelia™ *Candida* Ag and Ab showed an improvement of sensitivity (80.0%) and decrease of specificity (61.7%).

The ROC curves obtained from combination of RP-Ab/mannanemia (combined marker analysis by sera) showed a significant improvement of the diagnostic performances as reveled by AUCs: 0.902, 0.886, 0.884, 0.872, and 0.853 for Fba1, Hwp1, Hsp90, Eno1, and Mp65 respectively versus 0.769 for mannanemia and anti-mannan antibody combination (Table 5).

Furthermore, the association of RP-Ab and mannanemia increases significantly sensitivity and specificity. With a specificity arbitrarily fixed at 80.0% for the combination of mannan Ag+mannan Ab, sensitivities of mannan Ag+Hsp90, mannan Ag+Fba1 Ab, mannan Ag+Hwp1 Ab, mannan Ag+Eno1 Ab, and mannan Ag+Mp65 Ab were 80.9%, 83.8%, 83.8%, 79.1%, and 75.5%, respectively while the current serological diagnosis tests that combined mannan Ag+mannan Ab has a sensitivity of 61.7% (Table 5).

TABLE 5

Diagnosis potential (mROC approach) of RP-Ab associated with mannanemia for IC diagnosis.

| Combination of 2 biomarkers | AUC | Cut-off* | Se(%) | Sp(%) | PPV(%) | NPV(%) | CI95% |
|---|---|---|---|---|---|---|---|
| Mannan Ag* + Fba1 Ab* | 0.902 | −1.975 | 83.8 | 80.0 | 86.9 | 75.0 | [0.871; 0.927] |
| Mannan Ag* + Hwp1 Ab* | 0.886 | −2.629 | 83.8 | 80.0 | 87.2 | 75.2 | [0.851; 0.915] |
| Mannan Ag* + Hsp90 Ab* | 0.884 | −2.031 | 80.9 | 80.0 | 86.8 | 72.0 | [0.848; 0.911] |
| Mannan Ag* + Eno1 Ab* | 0.872 | −2.209 | 79.1 | 80.0 | 86.6 | 70.1 | [0.835; 0.901] |

TABLE 5-continued

Diagnosis potential (mROC approach) of RP-Ab associated with mannanemia for IC diagnosis.

| Combination of 2 biomarkers | AUC | Cut-off* | Se(%) | Sp(%) | PPV(%) | NPV(%) | CI95% |
|---|---|---|---|---|---|---|---|
| Mannan Ag* + Mp65 Ab* | 0.853 | −1.483 | 75.5 | 80.0 | 86.4 | 66.8 | [0.815; 0.885] |
| Mannan Ag* + Mannan Ab* | 0.769 | −0.869 | 61.7 | 80.0 | 83.8 | 56.3 | [0.723; 0.809] |

*Markers normalized by a log10 transform.
AUC: area under the curve; Se: sensibility; Sp: specificity; PPV: positive predictive value (measures the proportion of subjects with positive test results who are correctly diagnosed); NPV: negative predictive value (measures the proportion of subjects with negative test results who are correctly diagnosed); CI 95%: 95% confidence interval. The cut-off value was set in order to specificity to 80%.

Noteworthy, the contribution of mannanemia and RP-Ab association was significantly higher for *Candida parapsilosis* infected patients where RP-Ab reached a sensitivity of 67.2% versus 21.3% for anti-mannan antibodies. Such an improvement was also observed for episodes determined by *Candida albicans, Candida kruseï, Candida glabrata, Candida tropicalis* and *Candida lusitaniae*.

As compared with the combination of mannanemia with anti-mannan antibodies, mannanemia and RP-Ab combination improved specificity of detection of IC associated with *Geotrichum capitatum* or *Candida norvegiensis*.

Analysis of RP-Ab/Mannanemia for the Precocity of IC Diagnosis

The contribution of RP-Ab/mannanemia association to early diagnosis of IC was performed by considering only serum samples collected during the period day −15 and the day of isolation of yeasts species from blood culture (day of positivation of blood culture).

All combinations were able to significantly differentiate IC from Controls (p<0.0001) with higher values of AUC than mannan Ag/Ab mannan (Table 6).

Accordingly, all RP-Ab/mannanemia remained discriminant for IC even if no significant difference with mannanemia/anti-mannan antibody in terms of mean delay of positivity before blood culture (5-6 days before positive blood culture).

Determination of Diagnostic Odds Ratio of Different Antibody and Antigen Combination For the Diagnosis of IC Odds ratio reflect the scale of risk for developing IC according to the intensity of antibody response against RP and mannanemia levels. Knowing that the prognosis of IC is closely correlated with the delay of initiation of antifungal therapy, this ratio could help to identify patients that need an early antifungal treatment.

For all the associations of markers, 3 modalities of response intensity were determined in function of the repartition of values obtained in the cohort (using the quartile values as cutpoints). So, for each combination of markers the values of modality1 (mod1) are relative to the interval [Min, T1[($1^{st}$ tertile), the values of modality2 (mod2) are relative to the interval [T1, T2[($2^{nd}$ tertile) and the values of

TABLE 6

Analysis of biomarkers association performance in two weeks before isolation of yeasts from blood samples.

| Marker combinations | pWILCOX | pWILCOX_FDR | pWELCH | pWELCH_FDR | Nfold Median | AUC |
|---|---|---|---|---|---|---|
| Mannan Ag + Fba1 Ab | 0.0001 | 0.00011 | 0.00010 | 0.00012 | 2.06 | 0.892 |
| Mannan Ag + Hwp1 Ab | 0.0001 | 0.00011 | 0.00010 | 0.00012 | 1.63 | 0.872 |
| Mannan Ag + Hsp90 Ab | 0.0001 | 0.00011 | 0.00010 | 0.00012 | 1.64 | 0.871 |
| Mannan Ag + Eno1 Ab | 0.0001 | 0.00011 | 0.00010 | 0.00012 | 1.48 | 0.863 |
| Mannan Ag + Mp65 Ab | 0.0001 | 0.00011 | 0.00010 | 0.00012 | 1.63 | 0.826 |
| Mannan Ag + Mannan Ab | 0.0001 | 0.00011 | 0.00010 | 0.00012 | 1.19 | 0.719 |

Determination of mean day of positivity of different biomarkers was performed between day −15 and the day of isolation of yeast from blood samples. For all of these markers, the mean of positivity is between −5 and −6 days before the isolation of yeasts from blood samples.

TABLE 7

Determination of mean day of positivity of different RP-Ab and mannanemia association in comparison with the isolation day of yeasts in blood samples.

| Marker combinations | Mean (positive Day) |
|---|---|
| Mannan Ag + Mannan Ab | −5.05 |
| Mannan Ag + Fba1 Ab | −5.59 |
| Mannan Ag + Hsp90 Ab | −5.28 |
| Mannan Ag + Eno1 Ab | −5.48 |
| Mannan Ag + Hwp1 Ab | −5.41 |
| Mannan Ag + Mp65 Ab | −5.31 | modality3 (mod3) are relative to the interval [T2, Max[($3^{rd}$ tertile). The more the intensity of response is high, the more the risk of being IC is important.

The Anti-mannan antibody and mannanemia combination was associated with significant and adjusted Odds Ratios (OR) varying between 2,4 and 17.5. In comparison, the (Mp65 Ab and mannanemia) combination was associated with significant and adjusted Odds Ratios varying between 5.5 and 47.9. The (Eno1 Ab and mannanemia) combination was associated with significant and adjusted Odds Ratios varying between 7.7 and 59.4. The (Hwp1 Ab and mannanemia) combination was associated with significant and adjusted Odds Ratios varying between 7.1 and 65.5. The (Hsp90 Ab and mannanemia) combination was associated with significant and adjusted Odds Ratios varying between 6.8 and 77.5. The (Fba1 Ab and mannanemia) combination was associated with significant and adjusted Odds Ratios varying between 8.8 and 108.2 for (Tables 8-13).

TABLE 8

Determination of Odds Ratios on Mannan Ag + Mannan Ab according to the intensity of signals Odds Ratio Estimates

| Effect | Modality Interval | Point Estimate | 95% Wald Confidence Limits | |
|---|---|---|---|---|
| Mannan Ag + Mannan Ab mod2 vs mod1 | [0.05; 0.64[ vs [−2.19; 0.05[ | 2.414 | 1.519 | 3.838 |
| Mannan Ag + Mannan Ab mod3 vs mod1 | [0.64; 8.65[ vs [−2.19; 0.05[ | 17.485 | 9.041 | 33.817 |
| Mannan Ag + Mannan Ab mod3 vs mod2 | [0.64; 8.65[ vs [0.05; 0.64[ | 7.242 | 3.763 | 13.936 |

TABLE 9

Determination of Odds Ratios on Mannan Ag + Mp65 Ab according to the intensity of signals Odds Ratio Estimates

| Effect | Modality Interval | Point Estimate | 95% Wald Confidence Limits | |
|---|---|---|---|---|
| Mannan Ag + Mp65 Ab mod2 vs mod1 | [−0.09; 1.43[ vs [−6.89; −0.09[ | 5.456 | 3.324 | 8.956 |
| Mannan Ag + Mp65 Ab mod3 vs mod1 | [1.43; 10.37[ vs [−6.89; −0.09[ | 47.887 | 21.578 | 106.276 |
| Mannan Ag + Mp65 Ab mod3 vs mod2 | [1.43; 10.37[ vs [−0.09; 1.43[ | 8.777 | 3.979 | 19.360 |

TABLE 10

Determination of Odds Ratios on Mannan Ag + Eno1 Ab according to the ntensity of signals Odds Ratio Estimates

| Effect | Modality Interval | Point Estimate | 95% Wald Confidence Limits | |
|---|---|---|---|---|
| Mannan Ag + Eno1 Ab mod2 vs mod1 | [−0.30; 1.61[ vs [−3.75; −0.30[ | 7.739 | 4.613 | 12.983 |
| Mannan Ag + Eno1 Ab mod3 vs mod1 | [1.61; 20.74[ vs [−3.75; −0.30[ | 59.421 | 26.538 | 133.049 |
| Mannan Ag + Eno1 Ab mod3 vs mod2 | [1.61; 20.74[ vs [−0.30; 1.61[ | 7.678 | 3.466 | 17.011 |

TABLE 11

Determination of Odds Ratios on Mannan Ag + Hwp1 Ab according to the intensity of signals.

Odds Ratio Estimates

| Effect | Modality Interval | Point Estimate | 95% Wald Confidence Limits | |
|---|---|---|---|---|
| Mannan Ag + Hwp1 Ab mod2 vs mod1 | [−0.34; 1.90[ vs [−4.45; −0.34[ | 7.065 | 4.237 | 11.781 |
| Mannan Ag + Hwp1 Ab mod3 vs mod1 | [1.90; 11.66[ vs [−4.45; −0.34[ | 65.464 | 28.095 | 152.538 |
| Mannan Ag + Hwp1 Ab mod3 vs mod2 | [1.90; 11.66[ vs [−0.34; 1.90[ | 9.266 | 4.018 | 21.365 |

TABLE 12

Determination of Odds Ratios on Mannan Ag + Hsp90 according to the intensity of signals.

Odds Ratio Estimates

| Effect | Modality Interval | Point Estimate | 95% Wald Confidence Limits | |
|---|---|---|---|---|
| Mannan Ag + Hsp90 Ab mod2 vs mod1 | [−0.35; 1.89[ vs [−7.45; −0.35[ | 6.777 | 4.068 | 11.289 |
| Mannan Ag + Hsp90 Ab mod3 vs mod1 | [1.89; 12.40[ vs [−7.45; −0.35[ | 77.458 | 31.551 | 190.161 |
| Mannan Ag + Hsp90 Ab mod3 vs mod2 | [1.89; 12.40[ vs [−0.35; 1.89[ | 11.430 | 4.705 | 27.771 |

TABLE 13

Determination of Odds Ratios on Mannan Ag + Fba1 Ab according to the intensity of signals.

Odds Ratio Estimates

| Effect | Modality Interval | Point Estimate | 95% Wald Confidence Limits | |
|---|---|---|---|---|
| Mannan Ag + Fba1 Ab mod2 vs mod1 | [−0.39; 2.17[vs [−8.08; −0.39[ | 8.762 | 5.180 | 14.822 |
| Mannan Ag + Fba1 Ab mod3 vs mod1 | [2.17; 11.96[vs [−8.08; −0.39[ | 108.250 | 40.808 | 287.149 |
| Mannan Ag + Fba1 Ab mod3 vs mod2 | [2.17; 11.96[vs [−0.39; 2.17[ | 12.354 | 4.745 | 32.165 |

Thus, according to this scale, association of anti-mannan antibody and mannanemia allows a risk at a maximum of 17.5 while the risk obtained with the association with mannanemia and RP-Ab reaches 47.9, 59.4, 65.5, 77.5 and 108.2 for respectively Mp65, Eno1, Hwp1, Hsp90 and Fba1.

Performance of the Combined Interpretation of the Separated Biomarker Assays

The performance of the diagnosis method based on the combined interpretation of the separated biomarker assays, i.e. based on determining if an elevated level of said *Candida* glycan, and/or an elevated level of antibody directed against said *Candida* protein selected from the group consisting of Fba1, Eno1, Hsp90, Hwp1, and Mp65, relative to their respective reference level is detected, was evaluated both on sera and patients. In the evaluation on sera, it is evaluated if the biomarker levels measured in each serum sample of any patient correctly led to the identification of the patient as having or not having invasive candidiasis. In the evaluation on patients, it is evaluated if altogether the biomarker levels measured in sera samples of a given patient correctly led to the identification of the patient as having or not having invasive candidiasis.

The performances on sera using combined interpretation of separated assays, as detailed in Table 14, show that for a specificity set at 79.9% (about 80%) the levels of sensitivity obtained for the different biomarker combinations Mannan Ag+protein Ab, although not identical to those obtained on sera using the combined analysis of the biomarkers (results shown in Table 5), are all improved as compared with the reference test Mannan Ag+Mannan Ab.

TABLE 14

Performances on sera using combined interpretation of separated assays

| Markers | Sensitivity (%) | Specificity (%) |
|---|---|---|
| Mannan Ag + Hsp90 Ab | 74.8 | 79.9 |
| Mannan Ag + Mp65 Ab | 75.6 | 79.9 |
| Mannan Ag + Fba1 Ab | 83.5 | 79.9 |
| Mannan Ag + Eno1 Ab | 78.3 | 79.9 |
| Mannan Ag + Hwp1 Ab | 81.5 | 79.9 |
| Mannan Ag + Mannan Ab* | 62.6 | 75.1 |

*sensitivity and specificity values of the current Platelia *Candida* antigen (Ag) and Platelia *Candida* Ab Plus tests (Bio-Rad Laboratories, Marnes-La-Coquette, France).

The comparison of Table 14 and Table 15 shows that the performances on sera or on patients using combined interpretation of separated assays are similar.

TABLE 15

Performances on patients using combined interpretation of separated assays

| Markers | Sensitivity (%) | Specificity (%) |
|---|---|---|
| Mannan Ag + Hsp90 Ab | 80.6 | 79.9 |
| Mannan Ag + Mp65 Ab | 83.9 | 79.9 |
| Mannan Ag + Fba1 Ab | 84.9 | 79.9 |
| Mannan Ag + Eno1 Ab | 82.8 | 79.9 |
| Mannan Ag + Hwp1 Ab | 84.9 | 79.9 |
| Mannan Ag + Mannan Ab* | 61.3 | 75.1 |

*sensitivity and specificity values of the current Platelia *Candida* antigen (Ag) and Platelia *Candida* Ab Plus tests (Bio-Rad Laboratories, Marnes-La-Coquette, France).

The invention claimed is:

1. An in vitro method for diagnosing invasive candidiasis (IC) in a subject, said method comprising the steps:

a) detecting a level of a *Candida* mannan in a blood, plasma or serum sample of the subject using a method selected from the group consisting of an immunoassay, a chromatography, an enzyme-based chemoluminescent method, surface plasmon resonance, mass-spectrometry, and a lectin-based detection;

b) detecting by an immunoassay a level of antibodies directed against a *Candida* protein selected from the group consisting of fructose bisphosphate aldolase (Fba1), enolase 1 (Eno1), heat shock protein 90 (Hsp90), hyphal wall protein (Hwp1), and mannoprotein 65 (Mp65) in the same sample of the subject or in another sample sequentially obtained from the same subject, essentially simultaneously or no more than 3 hours apart;

c) performing a combined analysis of the level of said *Candida* mannan detected in step a) and the level of antibodies directed against said *Candida* protein detected in step b) by calculating a level of a marker $Z = \Sigma\ a_i \times [\text{Marker i}]$, wherein [Marker i] are individual levels of said *Candida* mannan and of the antibodies directed against said *Candida* protein, and $a_i$ are coefficients which values are determined in order to maximize an Area Under the Curve (AUC) of a Relative Operating Characteristic (ROC) curve for the combination of [Marker i]; and d) deducing that the subject is developing or has developed invasive candidiasis if the level of the marker Z calculated in step c) is higher than a reference level of marker Z.

2. The method according to claim 1, wherein at step b) the level of antibodies against Fba1, or antibodies against Eno1, or antibodies against Hsp90, or antibodies against Hwp1, or antibodies against Mp65, only, is detected.

3. The method according to claim 1, wherein said method does not comprise detecting an antibody directed against mannan.

4. The method according to claim 1, wherein said *Candida* mannan is detected by a sandwich enzyme immunoassay which uses, as capture and detection antibodies, an antibody recognizing sequences of α-linked oligomannoses comprising more than four residues.

5. The method according to claim 1, wherein said reference level of the marker Z is a single value or a range of values determined based on the level of said *Candida* mannan or the level of antibodies directed against said *Candida* protein, as appropriate, measured in a population of healthy subjects, in a population of subjects superficially infected with a *Candida* strain, in a population of subjects suffering from invasive candidiasis, or in a sample from the same subject obtained at an earlier time point.

6. The method according to claim 1, wherein invasive candidiasis is due to an infection with a *Candida* species selected from the group consisting of *Candida albicans, Candida parapsilosis, Candida kruseï, Candida tropicalis, Candida glabrata, Candida lusitaniae, Geotrichum capitatum,* and *Candida norvegiensis.*

7. The method according to claim 1, wherein in step b) the antibodies are directed against a *Candida* Fba1.

8. The method according to claim 7, wherein the level of the antibodies directed against the *Candida* Fba1 is detected using a polypeptide comprising:
    a) SEQ ID NO:2; or
    b) a variant polypeptide of the polypeptide defined in a), wherein said variant polypeptide has at least 80% sequence identity with the polypeptide defined in a), over the whole length of the polypeptide.

9. The method according to claim 1, wherein in step b) the antibodies are directed against a *Candida* Eno1.

10. The method according to claim 9, wherein the level of the antibodies directed against the *Candida* Eno1 is detected using a polypeptide comprising:
    a) SEQ ID NO:4; or
    b) a variant polypeptide of the polypeptide defined in a), wherein said variant polypeptide has at least 80% sequence identity with the polypeptide defined in a), over the whole length of the polypeptide.

11. The method according to claim 1, wherein in step b) the antibodies are directed against a *Candida* Hsp90.

12. The method according to claim 11, wherein the level of the antibodies directed against the *Candida* Hsp90 is detected using a polypeptide comprising:
    a) SEQ ID NO:6;
    b) amino acids at positions 313 to 707 of SEQ ID NO:6;
    c) a sequence SEQ ID NO:13, SEQ ID NO:14, SEQ ID NO:15, or SEQ ID NO:16; or
    d) a variant polypeptide of the polypeptide defined in a), b), or c), wherein said variant polypeptide has at least 80% sequence identity with the polypeptide defined in a), b), or
    c) over the whole length of the polypeptide.

13. The method according to claim 1, wherein in step b) the antibodies are directed against a *Candida* Hwp1.

14. The method according to claim 13, wherein the level of the antibodies directed against the *Candida* Hwp1 is detected using a polypeptide comprising:
    a) SEQ ID NO:8;
    b) amino acids at positions 41 to 200, or at positions 27 to 203 of SEQ ID NO:8; or
    c) a variant polypeptide of the polypeptide defined in a) or b), wherein said variant polypeptide has at least 80% sequence identity with the polypeptide defined in a) or b), over the whole length of the polypeptide.

15. The method according to claim 1, wherein in step b) the antibodies are directed against a *Candida* Mp65.

16. The method according to claim 15, wherein the level of the antibodies directed against the *Candida* Mp65 is detected using a polypeptide comprising:
    a) SEQ ID NO:10 or SEQ ID NO:12; or
    b) a variant polypeptide of the polypeptide defined in a), wherein said variant polypeptide has at least 80% sequence identity with the polypeptide defined in a), over the whole length of the polypeptide.

* * * * *